United States Patent
Kim et al.

(10) Patent No.: US 12,415,125 B2
(45) Date of Patent: Sep. 16, 2025

(54) METHOD FOR PROVIDING WORKOUT DATA USING A PLURALITY OF ELECTRONIC DEVICES AND ELECTRONIC DEVICES THEREFOR

(71) Applicant: Samsung Electronics Co., Ltd., Suwon-si (KR)

(72) Inventors: Hyeonseong Kim, Suwon-si (KR); Seongmin Je, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 286 days.

(21) Appl. No.: 17/893,644

(22) Filed: Aug. 23, 2022

(65) Prior Publication Data

US 2022/0401815 A1    Dec. 22, 2022

Related U.S. Application Data

(63) Continuation of application No. PCT/KR2022/007771, filed on May 31, 2022.

(30) Foreign Application Priority Data

May 31, 2021    (KR) .................. 10-2021-0070325

(51) Int. Cl.
*A61B 5/11*    (2006.01)
*A61B 5/00*    (2006.01)
(Continued)

(52) U.S. Cl.
CPC ........ *A63B 71/0622* (2013.01); *A61B 5/1114* (2013.01); *A61B 5/4561* (2013.01);
(Continued)

(58) Field of Classification Search
CPC .................. A63B 2220/803; A61B 5/4561
See application file for complete search history.

(56) References Cited

U.S. PATENT DOCUMENTS

| 9,248,340 B2 | 2/2016 | Hoffman et al. |
| 10,188,930 B2 | 1/2019 | Winsper et al. |

(Continued)

FOREIGN PATENT DOCUMENTS

| CA | 2 821 274 A1 | 6/2012 |
| JP | 2020-137566 A | 9/2020 |

(Continued)

OTHER PUBLICATIONS

International Search Report dated Sep. 6, 2022, issued in an International Application No. PCT/KR2022/007771.

(Continued)

*Primary Examiner* — John E Breene
*Assistant Examiner* — Alex T Devito
(74) *Attorney, Agent, or Firm* — Jefferson IP Law, LLP

(57) ABSTRACT

An electronic device is provided. The electronic device includes a display, a communication circuit, and at least one processor configured to recognize a user's initial posture based on at least one of motion sensor signals of a first external electronic device and a second external electronic device received through the communication circuit, control the first external electronic device to receive a first motion sensor signal, obtain the user's workout data based on the first motion sensor signal when the initial posture satisfies a designated condition, control the second external electronic device to receive a second motion sensor signal when the user's movement is not recognized based on the first motion sensor signal and obtain the user's workout data based on the second motion sensor signal, and provide the workout data through at least one of the display or the first external electronic device.

20 Claims, 15 Drawing Sheets

(51) Int. Cl.
  *A63B 71/06* (2006.01)
  *G01P 13/00* (2006.01)
  *G06F 3/14* (2006.01)

(52) U.S. Cl.
  CPC .............. *G01P 13/00* (2013.01); *G06F 3/14* (2013.01); *A63B 2071/0663* (2013.01); *A63B 2220/20* (2013.01); *A63B 2220/74* (2013.01); *A63B 2220/803* (2013.01)

(56) References Cited

U.S. PATENT DOCUMENTS

| | | | |
|---|---|---|---|
| 10,248,217 B2 | 4/2019 | Chang et al. | |
| 10,342,427 B2 | 7/2019 | Hwang et al. | |
| 2008/0258921 A1* | 10/2008 | Woo | G10H 1/40 482/8 |
| 2015/0100141 A1 | 4/2015 | Hughes | |
| 2016/0081625 A1* | 3/2016 | Kim | H04W 4/70 600/595 |
| 2016/0256082 A1 | 9/2016 | Ely et al. | |
| 2016/0367202 A1 | 12/2016 | Carter et al. | |
| 2017/0087414 A1 | 3/2017 | Aragones et al. | |
| 2019/0008449 A1 | 1/2019 | Samejima et al. | |
| 2019/0224529 A1 | 7/2019 | Jung et al. | |
| 2020/0376337 A1 | 12/2020 | Lee et al. | |
| 2021/0169417 A1 | 6/2021 | Burton | |

FOREIGN PATENT DOCUMENTS

| | | |
|---|---|---|
| KR | 10-2016-0035394 A | 3/2016 |
| KR | 10-2017-0083217 A | 7/2017 |
| KR | 10-2017-0129689 A | 11/2017 |
| KR | 10-2018-0021633 A | 3/2018 |
| KR | 10-1984565 B1 | 5/2019 |
| KR | 10-2009087 B1 | 8/2019 |
| KR | 10-2039616 B1 | 11/2019 |
| KR | 10-2020-0137460 A | 12/2020 |
| KR | 10-2293937 B1 | 8/2021 |

OTHER PUBLICATIONS

European Search Report dated Aug. 6, 2024, issued in European Application No. 22816444.8.

* cited by examiner

METHOD FOR PROVIDING WORKOUT DATA USING A PLURALITY OF ELECTRONIC DEVICES AND ELECTRONIC DEVICES THEREFOR

CROSS-REFERENCE TO RELATED APPLICATION(S)

This application is a continuation application, claiming priority under § 365(c), of an International application No. PCT/KR2022/007771, filed on May 31, 2022, which is based on and claims the benefit of a Korean patent application number 10-2021-0070325, filed on May 31, 2021, in the Korean Intellectual Property Office, the disclosure of each of which is incorporated by reference herein in its entirety.

TECHNICAL FIELD

The disclosure relates to a method for providing workout data using a plurality of electronic devices and an electronic device thereof.

BACKGROUND ART

With the development of technology, electronic devices are becoming smaller so that they may be easily carried, and are evolving to perform various functions in various forms of use according to user needs. Various types of wearable devices that may be used by being directly attached to a part of a user's body may be one of the electronic devices.

Recently, attempts have been actively made to obtain various information from the user's body movement by utilizing characteristics of a wearable device directly attached to a part of the user's body and to provide various services based thereon.

The above information is presented as background information only to assist with an understanding of the disclosure. No determination has been made, and no assertion is made, as to whether any of the above might be applicable as prior art with regard to the disclosure.

DISCLOSURE OF INVENTION

Technical Problem

Aspects of the disclosure are to address at least the above-mentioned problems and/or disadvantages and to provide at least the advantages described below. Accordingly, an aspect of the disclosure is to provide a method and electronic device for providing a user's workout data using a plurality of electronic devices.

Another aspect of the disclosure is to provide a method of obtaining a signal related to a user's movement by interworking and controlling sensors of a plurality of electronic devices and providing workout data according thereto, and an electronic device thereof.

Additional aspects will be set forth in part in the description which follows and, in part, will be apparent from the description, or may be learned by practice of the presented embodiments.

Solution to Problem

In accordance with an aspect of the disclosure, an electronic device is provided. The electronic device includes a display, a communication circuit, and at least one processor electrically connected to the display and the communication circuit, wherein the at least one processor is configured to recognize a user's initial posture based on at least one of motion sensor signals of a first external electronic device and a second external electronic device received through the communication circuit, to control the first external electronic device to receive a first motion sensor signal, and to obtain the user's workout data based on the first motion sensor signal when the initial posture satisfies a designated condition, to control the second external electronic device to receive a second motion sensor signal when the user's movement is not recognized based on the first motion sensor signal and to obtain the user's workout data based on the second motion sensor signal, and to provide the workout data through at least one of the display or the first external electronic device.

In accordance with another aspect of the disclosure, an electronic device is provided. The electronic device includes a display, a motion sensor, a communication circuit, and at least one processor electrically connected to the display, the motion sensor, and the communication circuit, wherein the at least one processor is configured to recognize a user's initial posture based on at least one of a motion sensor signal received through the motion sensor or a motion sensor signal of an external electronic device received through the communication circuit, to control the motion sensor to receive a first motion sensor signal, and to obtain the user's workout data based on the first motion sensor signal when the initial posture satisfies a designated condition, to control the external electronic device to receive a second motion sensor signal, and to obtain the user's workout data based on the second motion sensor signal when the user's movement is not recognized based on the first motion sensor signal, and to provide the workout data through the display.

In accordance with another aspect of the disclosure, a method of operating an electronic device is provided. The method includes recognizing a user's initial posture based on at least one of motion sensor signals obtained from each of a first external electronic device and a second external electronic device, obtaining, when the initial posture satisfies a designated condition, the user's workout data based on a first motion sensor signal obtained from the first external electronic device, obtaining, when the user's movement is not recognized based on the first motion sensor signal, the user's workout data based on a second motion sensor signal obtained from the second external electronic device, and providing the workout data through at least one of a display of the electronic device or a display of the first external electronic device.

Advantageous Effects of Invention

According to various embodiments, it is possible to more effectively obtain and provide various workout data according to a user's various movements using a plurality of electronic devices.

According to various embodiments, an acquisition performance of workout data according to various situations can be improved by adaptively controlling sensors of a plurality of electronic devices according to the user's various movements to obtain a user's movement-related signal and extracting workout data accordingly.

Further, various effects directly or indirectly identified through this document can be provided.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF DRAWINGS

The above and other aspects, features, and advantages of certain embodiments of the disclosure will be more apparent from the following the description taken in conjunction with the accompanying drawings, in which.

The same reference numerals are used to represent the same elements throughout the drawings.

MODE FOR THE INVENTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
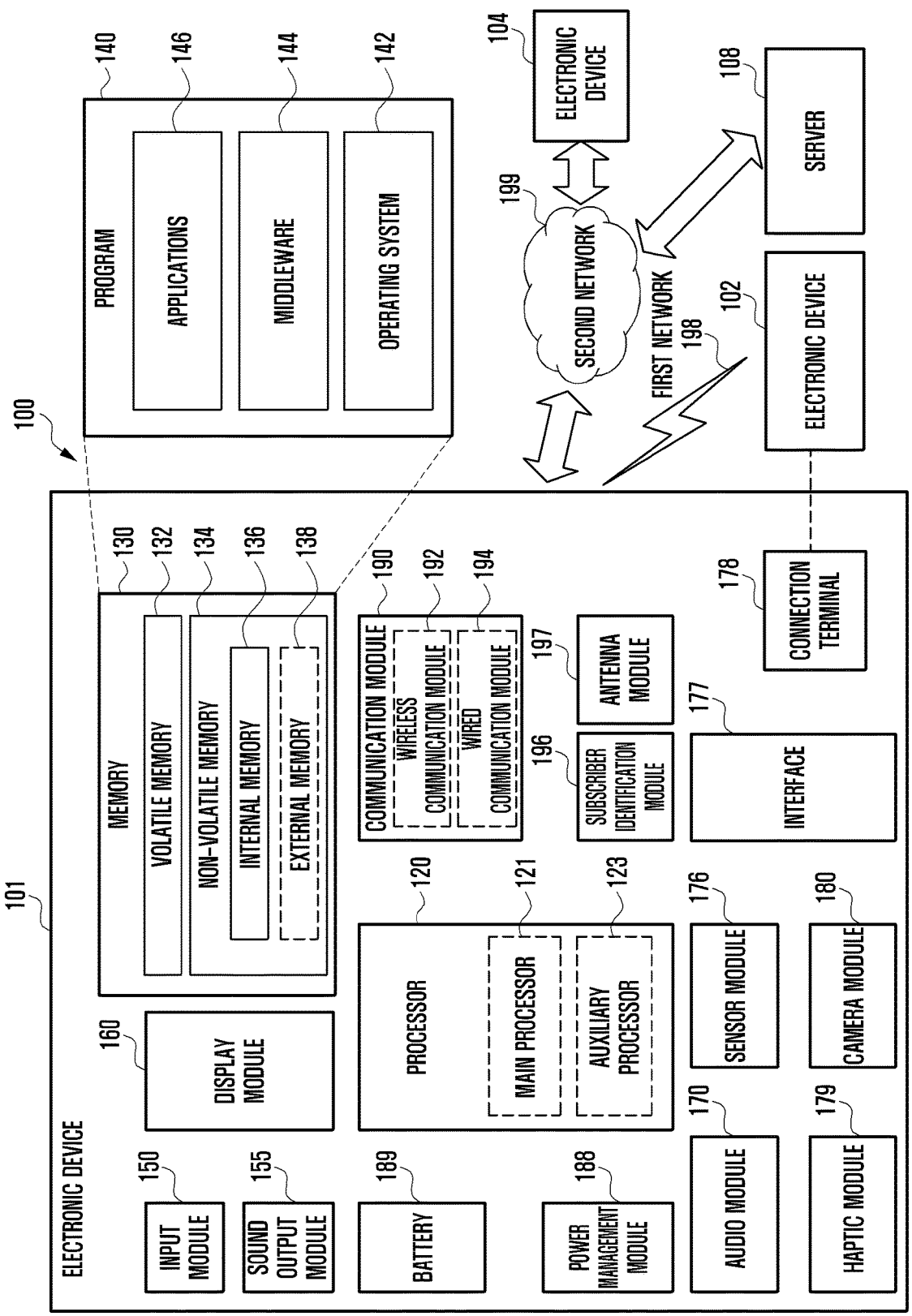
FIG. 1 is a block diagram illustrating an electronic device in a network environment according to an embodiment of the disclosure.

FIG. 1 is a block diagram illustrating an electronic device 101 in a network environment 100 according to an embodiment of the disclosure.

Referring to FIG. 1, the electronic device 101 in the network environment 100 may communicate with an electronic device 102 via a first network 198 (e.g., a short-range wireless communication network), or at least one of an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments, at least one of the components (e.g., the connecting terminal 178) may be omitted from the electronic device 101, or one or more other components may be added in the electronic device 101. In some embodiments, some of the components (e.g., the sensor module 176, the camera module 180, or the antenna module 197) may be implemented as a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thererto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. According to an embodiment, the display module 160 may include a touch sensor adapted to detect a touch, or a pressure sensor adapted to measure the intensity of force incurred by the touch.

The audio module 170 may convert a sound into an electrical signal and vice versa. According to an embodiment, the audio module 170 may obtain the sound via the input module 150, or output the sound via the sound output module 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a 5G network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., a printed circuit board (PCB)). According to an embodiment, the antenna module 197 may include a plurality of antennas (e.g., array antennas). In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

According to various embodiments, the antenna module 197 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 or 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In another embodiment, the external electronic device 104 may include an internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or healthcare) based on 5G communication technology or IoT-related technology.

The electronic device according to various embodiments may be one of various types of electronic devices. The electronic devices may include, for example, a portable communication device (e.g., a smailphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used in connection with various embodiments of the disclosure, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Figure 2:
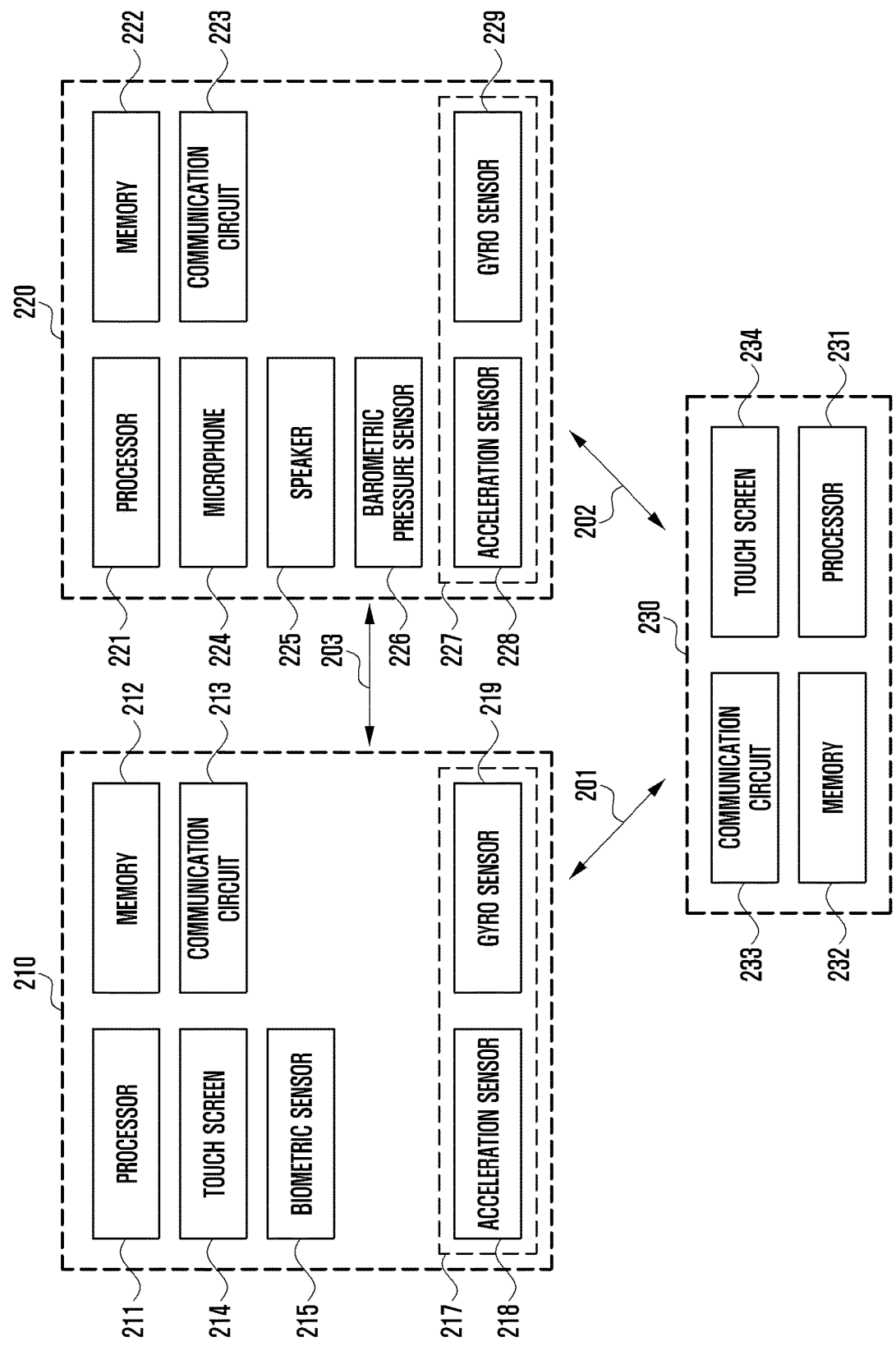
FIG. 2 is a block diagram illustrating a plurality of electronic devices according to an embodiment of the disclosure.

FIG. 2 is a block diagram illustrating a plurality of electronic devices (e.g., a first electronic device 210, a second electronic device 220, and/or a third electronic device 230) according to an embodiment of the disclosure.

Referring to FIG. 2, the first electronic device 210, the second electronic device 220, and/or the third electronic device 230 may include at least some of the components of the electronic device 101 of FIG. 1. According to various embodiments, the first electronic device 210 may be implemented as a wearable electronic device and include, for example, a watch-type wearable device such as a smart watch that has a communication function capable of communicating with the third electronic device 230 and that may be worn on a user's wrist. According to various embodiments, the second electronic device 220 may be implemented as a wearable electronic device (hereinafter, referred to as an earphone-type wearable device) that may be worn around the user's ear, such as augmented reality (AR) glasses or an ear bud. For example, the second electronic device 220 may include a headphone, an earphone, an ear bud, smart glasses, and/or AR glasses capable of providing a sound and/or video to the user based on audio data and/or video data received from a sound source electronic device (e.g., the third electronic device 230) through a communication function. Hereinafter, an example in which the first electronic device 210 is implemented into a smart watch and in which the second electronic device 220 is implemented into an ear bud will be described, but various embodiments may not be limited thereto.

According to various embodiments, the third electronic device 230 may be a portable electronic device and/or a mobile electronic device such as a smart phone, a tablet personal computer (PC), a portable multimedia player (PMP), a personal digital assistant (PDA), a laptop PC, and a wearable device.

According to various embodiments, the first electronic device 210 may include a processor 211 (e.g., the processor 120 of FIG. 1), a memory 212 (e.g., the memory 130 of FIG. 1), a communication circuit 213 (e.g., the communication module 190 of FIG. 1), a touch screen 214 (e.g., the display module 160 of FIG. 1), and a motion sensor 217 (e.g., the sensor module 176 of FIG. 1). According to an embodiment, the motion sensor 217 may include an acceleration sensor 218 and/or a gyro sensor 219. According to an embodiment, the first electronic device 210 may further include a biometric sensor 215 for obtaining a user's biometric information through a skin region in which blood vessels are positioned while maintaining at least a partial contact state with a human body. The components of each of the first electronic device 210, the second electronic device 220, and/or the third electronic device 230 illustrated in FIG. 2 are only an example, and some thereof may be omitted or substituted or integrated as one module according to various embodiments. A detailed description of repeated descriptions of the components described with reference to FIG. 1 among the components of each of the first electronic device 210, the second electronic device 220, and/or the third electronic device 230 illustrated in FIG. 2 may be omitted here.

According to various embodiments, the second electronic device 220 may include a processor 221 (e.g., the processor 120 of FIG. 1), a memory 222 (e.g., the memory 130 of FIG. 1), a communication circuit 223 (e.g., the communication module 190 of FIG. 1), a microphone 224 (e.g., the input module 150 of FIG. 1), a speaker 225 (e.g., the sound output module 155 of FIG. 1), and a motion sensor 227 (e.g., the sensor module 176 of FIG. 1). According to an embodiment, the second electronic device 220 may further include a touch sensor (not illustrated) configured to detect a touch. According to an embodiment, the motion sensor 227 may include an acceleration sensor 228 and/or a gyro sensor 229. According to an embodiment, the second electronic device 220 may further include a barometric pressure sensor 226 (e.g., the sensor module 176 of FIG. 1) for identifying a height from the ground according to barometric pressure measurement. According to an embodiment, the second electronic device 220 may obtain a sound through the microphone 224 to convert the sound into an electrical signal by the processor 221 or may output an electrical signal processed by the processor 221 based on audio data to the outside through the speaker 225. The components illustrated in FIG. 2 are only an example, and some thereof may be omitted or substituted or integrated as one module according to various embodiments. A detailed description of repeated descriptions of the components described with reference to FIG. 1 among the components illustrated in FIG. 2 may be omitted here.

According to various embodiments, the third electronic device 230 may include a processor 231 (e.g., the processor 120 of FIG. 1), a memory 232 (e.g., the memory 130 of FIG. 1), a communication circuit 233 (e.g., the communication module 190 of FIG. 1), and a touch screen 234 (e.g., the display module 160 of FIG. 1). The components illustrated in FIG. 2 are only an example, and some thereof may be omitted or substituted or integrated as one module according to various embodiments. A detailed description of repeated descriptions of the components described with reference to FIG. 1 among the components illustrated in FIG. 2 may be omitted here.

According to various embodiments, the processor 211, 221, or 231 may execute, for example, software (e.g., program), and control at least one other component (e.g., hardware or software component) of the first electronic device 210, the second electronic device 220, or the third electronic device 230 connected to the processor 211, 221, or 231, and perform various data processing or operations.

According to various embodiments, the memory 212, 222, or 232 may store various data used by at least one component (e.g., the processor 211, 221, or 231) or the motion sensor 217 or 227 of the first electronic device 210, the second electronic device 220, or the third electronic device 230. The data may include, for example, input data or output data for software (e.g., program) and a command related thereto. The memory 212, 222, or 232 may include a volatile memory or a non-volatile memory.

According to an embodiment, the memory 212, 222, or 232 may be coupled to the processor 211, 221, or 231 and/or the communication circuit 213, 223, or 233.

According to an embodiment, as at least a part of data processing or computation, the processor 211, 221, or 231 may load a command or data received from another component (e.g., the motion sensor 217 or 227 or the communication circuit 213, 223 or 233) into a volatile memory, process the command or data loaded into the volatile memory, and store result data in a non-volatile memory.

According to an embodiment, the communication circuit 213, 223, or 233 may support establishment of a communication channel through a communication link (e.g., a first communication link 201, a second communication link 202, or a third communication link 203) between the first electronic device 210, the second electronic device 220, or the third electronic device 230, and/or communication through the established communication channel.

According to an embodiment, the first electronic device 210 may directly connect with the second electronic device 220 through the third communication link 203 with various communication methods such as Bluetooth to transmit and receive a signal. According to another embodiment, the third electronic device 230 may connect with the first electronic device 210 and the second electronic device 220 through the first communication link 201 and the second communication link 202 with various communication methods such as Bluetooth to transmit and receive a signal.

According to an embodiment, the communication circuit 213, 223, or 233 may include a wireless communication module (e.g., cellular communication module, short-range wireless communication module, or global navigation satellite system (GNSS) communication module) or a wired communication module.

According to an embodiment, the communication circuit 213, 223, or 233 may enable the first electronic device 210 and/or the second electronic device 220 to communicate with the third electronic device 230 through the first communication link 201 or the second communication link 202 (e.g., a short-range radio communication network such as Bluetooth, WiFi direct, UWB, or infrared data association (IrDA)).

According to an embodiment, the communication circuit 213, 223, or 233 may enable the first electronic device 210 to communicate with the second electronic device 220 through a third communication link 203 (e.g., a short-range wireless communication network such as Bluetooth, WiFi direct, UWB, or infrared data association (IrDA)).

According to an embodiment, the communication circuit 213, 223, or 233 may include an antenna module (not illustrated). The antenna module of the communication circuit 213, 223 or 233 may transmit or receive a signal and/or power to and from the outside. According to an embodiment, the antenna module of the communication circuit 213, 223, or 233 may include one antenna including a radiator formed in a conductive pattern or a conductor formed on a substrate (e.g., PCB).

According to an embodiment, the motion sensor 217 or 227 may include an acceleration sensor 218 or 228 and a gyro sensor 219 or 229. The acceleration sensor 218 or 228 and/or the gyro sensor 219 or 229 may detect a movement and/or inertia of the first electronic device 210 or the second electronic device 220. The acceleration sensor 218 or 228 and/or the gyro sensor 219 or 229 may include a circuit (e.g., integrated circuit (IC)) that controls an operation of the acceleration sensor 218 or 228 and/or the gyro sensor 219 or 229. For example, the circuit (e.g., integrated circuit (IC))

that controls the operation of the acceleration sensor 218 or 228 and/or the gyro sensor 219 or 229 may be included in the first electronic device 210 or the second electronic device 220, and be implemented into the processor 211 or 221.

According to an embodiment, the processor 211 or 231 of the first electronic device 210 or the third electronic device 230 may calculate workout data based on a motion sensor signal obtained from the acceleration sensor 218 or 228 and/or the gyro sensor 219 or 229 of the motion sensor 217 or 227.

According to an embodiment, as the user performs exercise, the third electronic device 230 may control the first electronic device 210 and the second electronic device 220 to obtain workout data. In this case, the first electronic device 210 and/or the second electronic device 220 may obtain motion information according to the user's exercise under the control of the third electronic device 230 to transmit the motion information to the third electronic device 230. In this case, the third electronic device 230 may communicate with the first electronic device 210 and/or the second electronic device 220 using the first communication link 201 and/or the second communication link 202 (e.g., the first network 198 of FIG. 1) including a short-range communication network such as Bluetooth (or BLE), WiFi direct, ultra wide band (UWB), or infrared data association (IrDA).

According to various embodiments, the processor 231 of the third electronic device 230 may control the first electronic device 210 and/or the second electronic device 220 to receive a motion sensor signal from the first electronic device 210 and/or the second electronic device 220 and recognize the user's initial posture based on the received motion sensor signal. The processor 231 may calculate, for example, a motion value and/or a posture value based on a motion sensor signal received from the first electronic device 210 and/or the second electronic device 220, and compare the motion value and/or the posture value with a threshold value and/or a configuration value to determine whether the initial posture satisfies a designated condition.

According to various embodiments, in order to obtain workout data, the processor 231 of the third electronic device 230 may control the first electronic device 210 to receive a motion sensor signal obtained by the motion sensor 217 of the first electronic device 210 or may control the second electronic device 220 based on the motion sensor signal from the first electronic device 210 to receive a motion sensor signal obtained by the motion sensor 227 of the second electronic device 220.

According to various embodiments, the first electronic device 210 may detect a movement of the first electronic device 210 through various types of sensors capable of detecting a movement of the first electronic device 210 such as the gyro sensor 219 and/or the acceleration sensor 218 included in the motion sensor 217 to provide a generated sensor value (e.g., motion sensor signal) to the third electronic device 230 through the communication circuit 213.

According to various embodiments, the second electronic device 220 may detect a movement of the second electronic device 220 through various types of sensors capable of detecting a movement of the second electronic device 220 such as the gyro sensor 229 and/or the acceleration sensor 228 included in the motion sensor 227 to provide a generated sensor value (e.g., motion sensor signal) to the third electronic device 230 through the communication circuit 223.

According to various embodiments, the processor 231 of the third electronic device 230 may obtain workout data based on a motion sensor signal received from the motion sensor 217 of the first electronic device 210 to recognize the user's motion.

According to various embodiments, when motion recognition is impossible by a motion sensor signal received from the first electronic device 210, the processor 231 of the third electronic device 230 may control the second electronic device 220 to receive a motion sensor signal from the second electronic device 220 and to obtain workout data based on the received motion sensor signal, thereby performing the user's motion recognition.

According to various embodiments, the processor 231 of the third electronic device 230 may obtain the user's workout data from a motion sensor signal received from the first electronic device 210 and/or a motion sensor signal received from the second electronic device 220. For example, the processor 231 of the third electronic device 230 may analyze the motion sensor signal to calculate workout data including an exercise time, the number of exercise, an exercise speed, and/or exercise calories.

According to various embodiments, the processor 231 of the third electronic device 230 may provide various information such as a guide for obtaining workout data and/or the obtained user's workout data through the touch screen 234. According to an embodiment, the processor 231 of the third electronic device 230 may receive a user input through the touch screen 234.

According to various embodiments, the touch screen 234 of the third electronic device 230 may provide various visual information related to workout data acquisition by the processor 231. For example, the touch screen 234 may display various visual information generated based on the workout data or a required visual notification in relation to acquisition of workout data.

According to various embodiments, the processor 231 of the third electronic device 230 may load an application for obtaining workout data stored in the memory 232 and perform operations for obtaining workout data in association with the first electronic device 210 and/or the second electronic device 220.

According to another embodiment, as the user performs exercise, the first electronic device 210 may obtain motion information according to the user's exercise from a motion sensor signal obtained by the motion sensor 217 thereof or may request a motion sensor signal to the second electronic device 220 to obtain motion information from the received motion sensor signal, thereby obtaining the user's workout data. In this case, the first electronic device 210 may communicate directly with the second electronic device 220 using the third communication link 203 (e.g., the first network 198 of FIG. 1) including a short-range communication network such as Bluetooth (or BLE), WiFi direct, ultra wide band (UWB), or infrared data association (IrDA).

According to various embodiments, in order to obtain workout data, the processor 211 of the first electronic device 210 may receive a motion sensor signal through the motion sensor 217 or receive a motion sensor signal from the second electronic device 220.

According to various embodiments, the motion sensor 217 of the first electronic device 210 may provide a sensor value (e.g., motion signal) generated according to movement detection of the first electronic device 210 to the processor 211 through various types of sensors capable of recognizing a movement of the first electronic device 210 such as the gyro sensor 219 and/or the acceleration sensor 218.

According to various embodiments, the processor 211 of the first electronic device 210 may recognize the user's motion through a motion sensor signal received from the motion sensor 217 of the first electronic device 210.

According to various embodiments, when motion recognition is impossible by a motion sensor signal received from the first electronic device 210, the processor 211 of the first electronic device 210 may request motion recognition to the second electronic device 220 and receive a motion sensor signal from the second electronic device 220.

According to various embodiments, the motion sensor 227 of the second electronic device 220 may detect a movement of the second electronic device 220 to provide a generated sensor value (e.g., motion signal) to the first electronic device 210 through various types of sensors capable of detecting a movement of the second electronic device 220 such as the gyro sensor 219 and/or the acceleration sensor 218 according to the control of the processor 221.

According to various embodiments, the processor 211 of the first electronic device 210 may obtain the user's workout data from a motion sensor signal of the first electronic device 210 received from the motion sensor 217 and/or a motion sensor signal received from the second electronic device 220. For example, the processor 211 of the first electronic device 210 may analyze a motion sensor signal to calculate workout data including an exercise time, the number of exercise, an exercise speed, and/or exercise calories.

According to various embodiments, the processor 211 of the first electronic device 210 may provide various information such as a guide for obtaining workout data and/or the obtained user's workout data through the touch screen 214. According to an embodiment, the processor 211 of the first electronic device 210 may receive a user input through the touch screen 214.

According to various embodiments, the touch screen 214 of the first electronic device 210 may provide various visual information related to workout data acquisition by the processor 211. For example, the touch screen 214 may display various visual information generated based on the workout data or a required visual notification in relation to acquisition of workout data.

According to various embodiments, the processor 211 of the first electronic device 210 may load an application for obtaining workout data stored in the memory 212 and enable to perform operations for obtaining workout data in association with the second electronic device 220.

Figure 3:
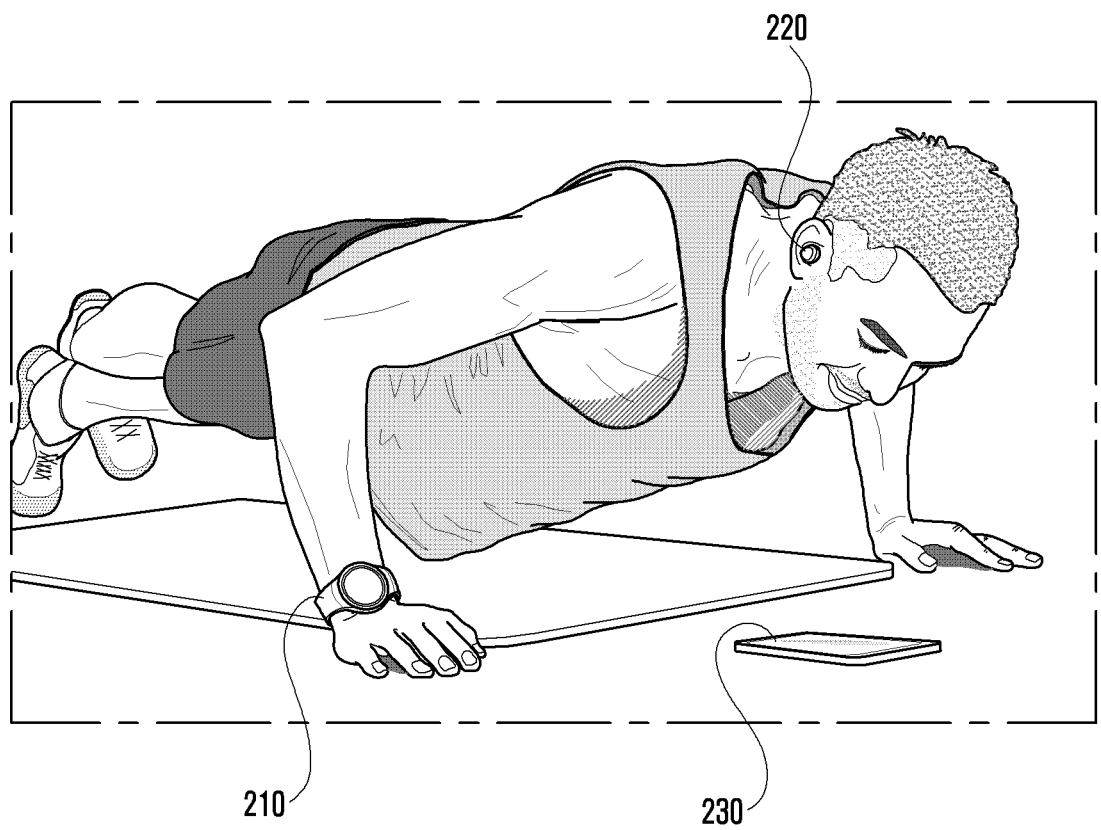
FIG. 3 is a conceptual diagram illustrating a method of obtaining a user's workout data using a plurality of electronic devices according to an embodiment of the disclosure.

FIG. 3 is a conceptual diagram illustrating a method of obtaining a user's workout data using a plurality of electronic devices according to an embodiment of the disclosure.

Referring to FIG. 3, a user may wear the first electronic device (e.g., the first electronic device 210 of FIG. 2) implemented as a watch-type wearable device on a wrist, wear the second electronic device (e.g., the second electronic device 220 of FIG. 2) implemented as an earphone type wearable device on the ear, and perform exercise. In this case, the user may position the third electronic device (e.g., the third electronic device 230 of FIG. 2) in the vicinity of the user to identify information and/or various notifications according to function execution of various apps including an exercise app for obtaining and providing workout data.

Referring to FIG. 3, in order to perform push-up exercise, the user may hold an initial posture and perform push-up exercise. In an embodiment, push-up exercise is described as an example, but the type of exercise is not limited thereto, and may be applied to various types of exercises in which a part of a body is fixed and in which a movement of another body part is regularly repeated, such as a pull-up or an inverted row.

According to an embodiment, the electronic device (e.g., the electronic device 101 of FIG. 1 or the electronic device 230 of FIG. 2) may include a display (e.g., the display module 160 of FIG. 1 or the touch screen 234 of FIG. 2), a communication circuit (e.g., the communication module 190 of FIG. 1 or the communication circuit 233 of FIG. 2), and at least one processor (e.g., the processor 120 of FIG. 1 or the processor 231 of FIG. 2) electrically connected to the display and the communication circuit, and the at least one processor may be configured to recognize the user's initial posture based on at least one of the first external electronic device (e.g., the first electronic device 210 of FIG. 2) or the second external electronic device (e.g., the second electronic device 220 of FIG. 2) received through the communication circuit, to control the first external electronic device to receive a first motion sensor signal when the initial posture satisfies a designated condition, to obtain the user's workout data based on the first motion sensor signal, to control the second external electronic device to receive a second motion sensor signal when the user's movement is not recognized based on the first motion sensor signal, to obtain the user's workout data based on the second motion sensor signal, and to provide the workout data through at least one of the display or the first external electronic device.

According to an embodiment, the first external electronic device and the second external electronic device may be configured to obtain the first motion sensor signal and the second motion sensor signal, respectively according to the user's movement at different positions among the user's body parts.

According to an embodiment, the designated condition of the initial posture is determined based on at least one of motion sensor signals of the first external electronic device and the second external electronic device, but may include at least one of a condition that the user's movement stops for a specified time or a condition that the designated posture value is maintained.

According to an embodiment, when the user's exercise is not recognized based on the first motion sensor signal, the processor may be configured to transmit a trigger signal requesting to obtain the second motion sensor signal to the second external electronic device.

According to an embodiment, the processor may perform coordinate transformation of the first motion sensor signal or the second motion sensor signal, extract a U-axis signal component, and detect a zero crossing point for the U-axis signal.

According to an embodiment, the processor may detect a zero-crossing section between consecutive zero-crossing points, calculate a peak and a valley within the zero-crossing section, and count the zero-crossing section as the number of one exercise when each of the calculated zero-crossing section, the peak, and the valley is within a designated range.

According to an embodiment, when the user's movement is not recognized based on the second motion sensor signal, the processor may be configured to identify whether the first external electronic device and the second external electronic device provide an UWB ranging function, to perform UWB ranging between the first external electronic device and the second external electronic device to obtain distance information, if the first external electronic device and the second external electronic device provide an UWB ranging function, and to obtain the user's workout data based on the distance information.

According to an embodiment, when the user's movement is not recognized based on the second motion sensor signal, the processor may be configured to receive a barometric pressure sensor signal through the barometric pressure sensor of the second external electronic device and to obtain the user's workout data based on the barometric pressure sensor signal.

According to an embodiment, the electronic device (e.g., the first electronic device 210 of FIG. 2) includes a display (e.g., the touch screen 214 of FIG. 2), a motion sensor (e.g., the motion sensor 219 of FIG. 2), a communication circuit (e.g., the communication circuit 213 of FIG. 2), and at least one processor (e.g., the processor 211 of FIG. 2) electrically connected to the display, the motion sensor, and the communication circuit, and the at least one processor may be configured to recognize the user's initial posture based on at least one of a motion sensor signal received through the motion sensor or a motion sensor signal of an external electronic device (e.g., the second electronic device 220 of FIG. 2) received through the communication circuit, to control the motion sensor to receive a first motion sensor signal when the initial posture satisfies a designated condition, to obtain the user's movement data based on the first motion sensor signal, to control the external electronic device to receive a second motion sensor signal when the user's movement is not recognized based on the first motion sensor signal, to obtain the user's workout data based on the second motion sensor signal, and to provide the workout data through the display.

According to an embodiment, the motion sensor and the second external electronic device may be configured to obtain the first motion sensor signal and the second motion sensor signal, respectively according to the user's movement at different positions among the user's body parts.

According to an embodiment, the designated condition of the initial posture is determined based on at least one of motion sensor signals of the motion sensor and the external electronic device, but may include at least one of a condition that the user's movement is stopped or a condition that a designated posture value is maintained for a specified time.

According to an embodiment, when the user's exercise is not recognized based on the first motion sensor signal, the processor may be configured to transmit a trigger signal requesting to obtain the second motion sensor signal to the external electronic device.

According to an embodiment, the processor may perform coordinate transformation of the first motion sensor signal or the second motion sensor signal, extract a U-axis signal component, and detect a zero crossing point for the U-axis signal.

According to an embodiment, the processor may detect a zero-crossing section between consecutive zero-crossing points, calculate a peak and a valley within the zero-crossing section, and count the zero-crossing section as the number of one exercise when each of the calculated zero-crossing section, the peak, and the valley is within a designated range.

According to an embodiment, when the user's movement is not recognized based on the second motion sensor signal, the processor may be configured to identify whether the external electronic device provides an UWB ranging function through the communication circuit, to perform UWB ranging with the external electronic device through the communication circuit to obtain distance information when the external electronic device provides UWB ranging, and to obtain the user's workout data based on the distance information.

According to an embodiment, when the user's movement is not recognized based on the second motion sensor signal, the processor may be configured to receive a barometric pressure sensor signal through the barometric pressure sensor of the second external electronic device and to obtain the user's workout data based on the barometric pressure sensor signal.

Figure 4:
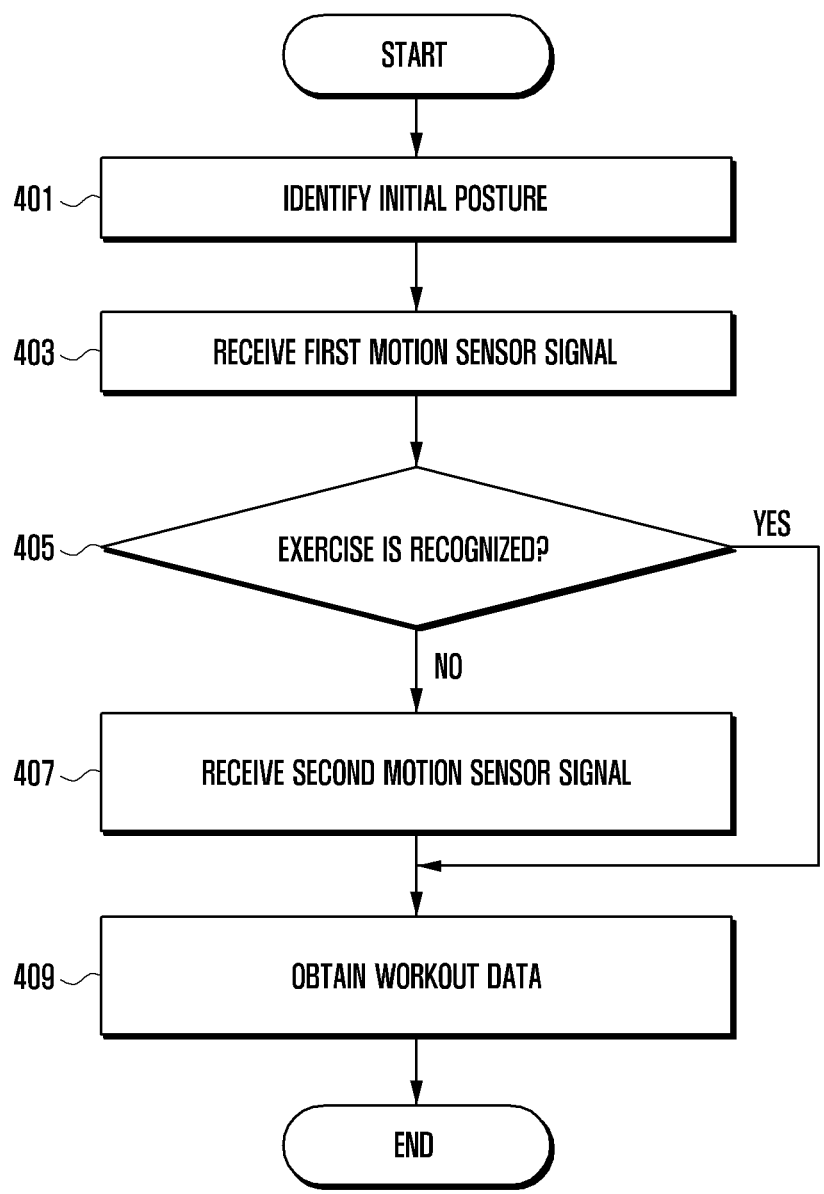
FIG. 4 is a flowchart illustrating a method of providing a user's workout data according to an embodiment of the disclosure.

FIG. 4 is a flowchart illustrating a method of obtaining a user's workout data according to an embodiment of the disclosure.

Referring to FIG. 4, the processor (e.g., the processor 211 or processor 231 of FIG. 2) of the first electronic device (e.g., the first electronic device 210 of FIG. 2) or the third electronic device (e.g., the third electronic device 230 of FIG. 2) may calculate workout data based on the motion sensor signal obtained from the acceleration sensor (e.g., the acceleration sensor 218 or 228 of FIG. 2) and/or the gyro sensor (e.g., the gyro sensor 219 or 229 of FIG. 2) of the motion sensor (e.g., the motion sensor 217 or 227 of FIG. 2) of the first electronic device 210 or the second electronic device (e.g., the second electronic device 220 of FIG. 2).

According to an embodiment, the processor 211 or 231 of the first electronic device 210 or the third electronic device 230 may calculate workout data based on a motion sensor signal obtained from the acceleration sensor 218 or 228 and/or the gyro sensor 219 or 229 of the motion sensor 217 or 227.

According to an embodiment, the first electronic device 210 may directly connect with the second electronic device 220 through the third communication link 203 with various communication methods such as Bluetooth to transmit and receive a signal. According to another embodiment, the third electronic device 230 may connect with the first electronic device 210 and the second electronic device 220 to transmit and receive a signal through the first communication link 201 and the second communication link 202 with various communication methods such as Bluetooth.

According to various embodiments, in operation 401, the processor 211 or 231 may recognize the validity of an initial posture for starting exercise based on a motion sensor signal obtained from the motion sensor 217 or 227.

According to an embodiment, a condition of a valid initial posture may include a state in which a user stops a movement for a predetermined time and takes an initial setup posture for starting exercise.

According to an embodiment, the processor 211 or 231 may determine the validity of the initial posture based on whether a movement is stopped for a predetermined time and/or a designated posture value is maintained. For example, in the case of push-up exercise, a posture facing the ground with a hand on the floor and a body facing down may be taken as an initial posture, the user may identify a posture value measured by placing the hand on the floor in a motion stop state based on a motion sensor signal from the first electronic device 210 worn on a wrist, and identify a posture value measured by viewing the ground in a motion stop state based on a motion sensor signal from the second electronic device 220 worn on the ear.

According to an embodiment, the processor 211 or 231 may recognize the validity of the initial posture based on motion sensor signals from the motion sensor 217 of the first electronic device 210 and the motion sensor 227 of the second electronic device 220.

According to an embodiment, the first electronic device 210 or the third electronic device 230 may receive an input of an execution command of an exercise app through the touch screen (e.g., the touch screen 214 or 234 of FIG. 2) or may receive an input of an exercise start command, and accordingly, may start operation 401 for obtaining workout data. According to an embodiment, the first electronic device 210 or the third electronic device 230 may receive an input for selecting one of exercise items provided on the executed exercise app through the touch screen 214 or 234.

According to an embodiment, in a state in which there is no significant movement based on the motion sensor signal obtained from the sensor module 217 or 227, when it is identified that the user's heart rate is rising based on a biometric sensor signal of the biometric sensor 215, the processor 211 or 231 may determine that the user is performing exercise and start an operation for obtaining workout data.

According to an embodiment, in this case, the processor 211 or 231 may determine the validity of the initial posture based on whether a movement is stopped for a predetermined time. For example, when the movement is stopped based on the motion sensor signal obtained from the sensor modules 217 and 227 of the first electronic device 210 and the second electronic device 220 for a predetermined time after an exercise app is executed or an exercise start command is executed, the processor 211 or 231 may determine that the initial posture is valid, and perform an operation for obtaining workout data.

According to an embodiment, as an exercise item is configured or identified, the processor 211 or 231 may connect to the first electronic device 210 and/or the second electronic device 220 with various communication methods such as Bluetooth, and identify the validity of the initial posture.

According to various embodiments, in operation 403, as the validity of the initial posture is identified, the processor 211 or 231 may start a workout data acquisition operation and receive a first motion sensor signal from the motion sensor 217 of the first electronic device 210.

According to various embodiments, in operation 405, the processor 211 or 231 may identify whether a motion is recognized based on the first motion sensor signal. In the case of exercise difficult to measure by the motion sensor 217 of the first electronic device 210, such as exercise having a small or insignificant movement of the arm according to an exercise item, a motion may not be recognized by the first electronic device 210 worn on the wrist. For example, when a movement is insignificant based on the first motion sensor signal obtained by the sensor module 217 of the first electronic device 210 and the user's heart rate does not rise based on the biometric sensor signal of the biometric sensor 215, the processor 211 or 231 may determine that there is no user's movement. For example, even if a movement is insignificant based on the first motion sensor signal obtained by the sensor module 217 of the first electronic device 210, when the user's heart rate rises based on the biometric sensor signal of the biometric sensor 215, the processor 211 or 231 may determine that there is the user's movement.

According to an embodiment, when an exercise item is selected, if the corresponding exercise item is an exercise item difficult to be recognized by the first electronic device 210 worn on the wrist, the processor 211 or 231 may drive the biometric sensor 215 to identify whether there is a user's movement. For example, in the case of an exercise item difficult to be recognized by the first electronic device 210, the processor 211 or 231 may identify whether the user's exercise is actually being performed based on a sensor signal of the biometric sensor 215.

According to various embodiments, when a motion is not recognized based on the first motion sensor signal, the processor 211 or 231 may enable the second electronic device 220 to drive the motion sensor 227 to receive an obtained second motion sensor signal in operation 407.

According to an embodiment, the processor 211 or 231 may control the second electronic device 220 to drive the motion sensor 227 to obtain the second motion sensor signal, and accordingly the processor 221 of the second electronic device 220 may drive the motion sensor 227 to obtain a second motion sensor signal, and transmit the second motion sensor signal to the first electronic device 210 or the third electronic device 230.

According to various embodiments, in operation 409, the processor 211 or 231 may obtain workout data based on the received first motion sensor signal or second motion sensor signal.

According to an embodiment, in the case of exercise in which an arm movement is large according to an exercise item, a motion may be recognized by the first electronic device 210 worn on the wrist. For example, when a motion is recognized by performing various exercise items in which an arm is moved by the first electronic device 210 worn on the wrist, the motion may be recognized by the first electronic device 210, and accordingly workout data may be obtained based on the first motion sensor signal.

According to an embodiment, in the case of exercise in which a movement of the arm is small or insignificant according to an exercise item, a motion may not be recognized by the first electronic device 210 worn on the wrist. For example, when a motion is not recognized due to a fixed movement of an arm part in the first electronic device 210 worn on the wrist, the second electronic device 220 may recognize a motion according to an action of fixing the arm part and moving a torso, and accordingly, workout data may be obtained based on the second motion sensor signal.

According to an embodiment, the processor 211 or 231 may process a first motion sensor signal or a second motion sensor signal to obtain workout data such as the number of exercises, an exercise time, an exercise speed, or exercise calories. For example, the number of exercises may be obtained by counting one repetition period as one time by analyzing a signal change pattern based on the first motion sensor signal or the second motion sensor signal. For example, the exercise time may be calculated from a time in which it is determined that a motion is recognized and exercise is thus started based on the first motion sensor signal or the second motion sensor signal to a time in which it is determined that the exercise is finished because a motion is not recognized for a certain time or more. For example, the exercise speed may be calculated as the total number of exercises for a total exercise time based on the first motion sensor signal or the second motion sensor signal. For example, exercise calories may be calculated with reference to known calories consumed for a corresponding exercise item in consideration of an exercise time and the number of exercises.

Figure 5:
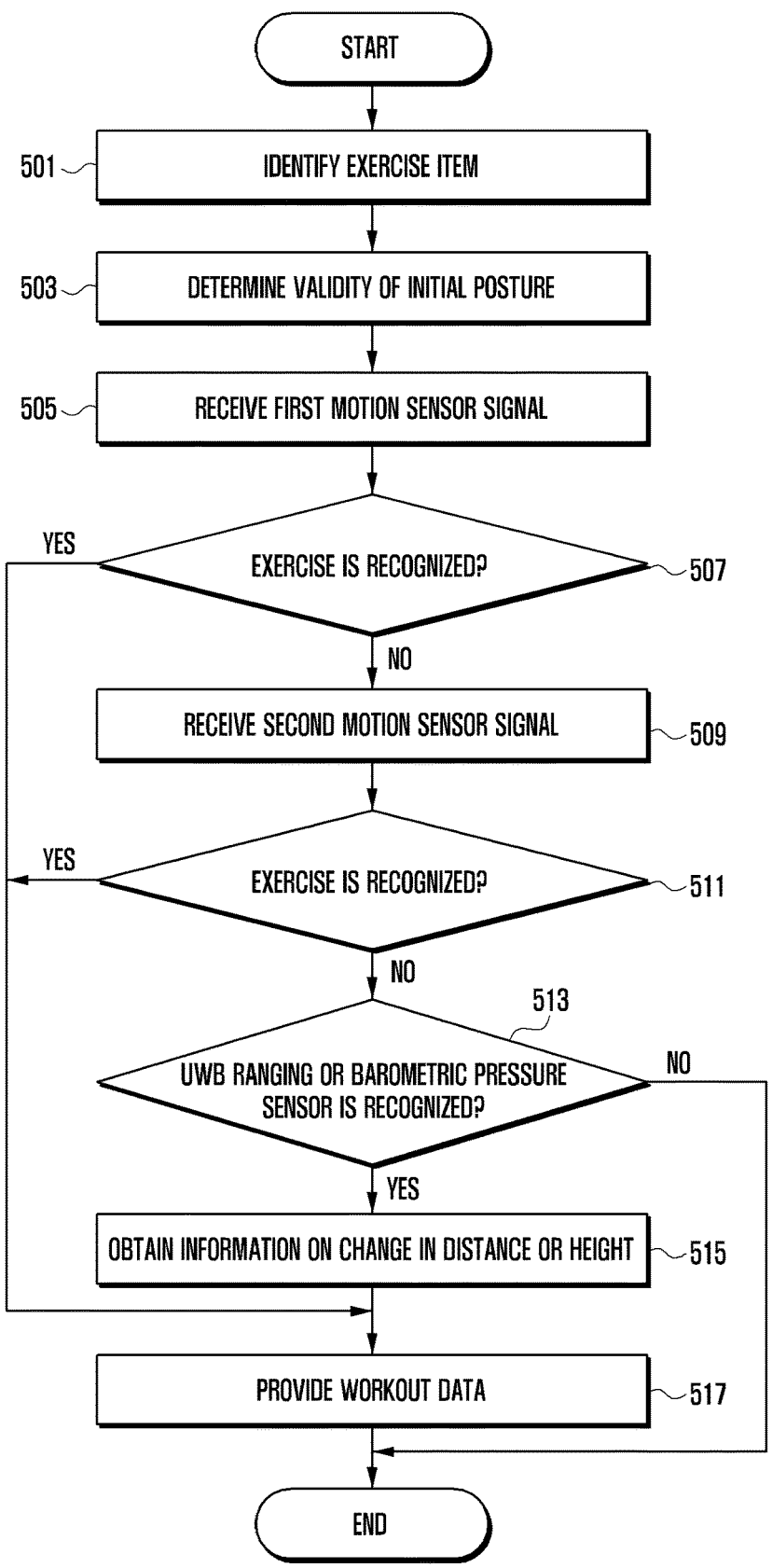
FIG. 5 is a flowchart illustrating a method of providing a user's workout data according to an embodiment of the disclosure.

FIG. 5 is a flowchart illustrating a method of providing a user's workout data according to an embodiment of the disclosure.

Referring to FIG. 5, the processor (e.g., the processor 211 or the processor 231 of FIG. 2) of the first electronic device (e.g., the first electronic device 210 of FIG. 2) or the third electronic device (e.g., the third electronic device 230 of FIG. 2) may calculate workout data based on a motion sensor signal obtained from the acceleration sensor (e.g., the acceleration sensor 218 or 228 of FIG. 2) and/or the gyro sensor (e.g., the gyro sensor 219 or 229 of FIG. 2) of the sensor module (e.g., the motion sensor 217 or 227 of FIG. 2) of the first electronic device 210 or the second electronic device (e.g., the second electronic device 220 of FIG. 2).

According to an embodiment, when the processor 211 or 231 of the first electronic device 210 or the third electronic device 230 may not calculate workout data based on a motion sensor signal obtained from the sensor module 217 or 227, the processor 211 or 231 may calculate workout data based on UWB ranging or sensing data of an barometric pressure sensor (e.g., the barometric pressure sensor 226 of FIG. 2).

According to an embodiment, the processor 211 or 231 of the first electronic device 210 or the third electronic device 230 may calculate workout data based on the motion sensor signal obtained from the acceleration sensor 218 or 228 and/or the gyro sensor 219 or 229 of the sensor module 217 or 227.

According to an embodiment, the first electronic device 210 may directly connect with the second electronic device 220 through the third communication link 203 with various communication methods such as Bluetooth to transmit and receive a signal. According to another embodiment, the third electronic device 230 may connect with the first electronic device 210 and the second electronic device 220 through the first communication link 201 and the second communication link 202 with various communication methods such as Bluetooth to transmit and receive a signal.

According to various embodiments, in operation 501, the processor 211 or 231 may identify an exercise item for providing workout data. For example, the first electronic device 210 or the third electronic device 230 may receive an input of an exercise item from the user through a touch screen (e.g., the touch screen 214 or 234 of FIG. 2). For example, the exercise item may include an exercise item in which a specific part of the user's body is fixed and another part thereof is repeatedly moved, such as a push-up, a pull-up, or an inverted row. According to an embodiment, when it is identified that the user's heart rate is increasing based on the biometric sensor signal of the biometric sensor 215 in a state in which there is no significant movement based on the motion sensor signal obtained from the sensor module 217 or 227, the processor 211 or 231 may determine that the user is performing fitness exercise, and identify the exercise item.

According to various embodiments, in operation 503, the processor 211 or 231 may recognize the validity of an initial posture for starting exercise based on a motion sensor signal obtained from the sensor module 217 or 227. According to an embodiment, after identifying an exercise item, the processor 211 or 231 may connect to the first electronic device 210 and/or the second electronic device 220 and receive a motion sensor signal with various communication methods such as Bluetooth, thereby identifying the validity of the initial posture.

According to an embodiment, the processor 211 or 231 may determine the validity of the initial posture based on whether a movement is stopped for a predetermined time and whether a designated posture value is maintained. For example, in the case of push-up exercise, a posture facing the ground with a hand on the floor and a body facing down may be configured as an initial posture. In this case, when a posture value measured by placing the hand on the floor in a motion stop state is identified based on the motion sensor signal from the first electronic device 210 worn on the wrist, and when a posture value measured by viewing the ground in a motion stop state is identified based on the motion sensor signal from the second electronic device 220 worn on the ear, the validity of the initial posture may be recognized.

According to various embodiments, in operation 505, as the validity of the initial posture is identified, the processor 211 or 231 may drive the motion sensor 217 of the first electronic device 210 to receive the first motion sensor signal.

According to various embodiments, in operation 507, the processor 211 or 231 may identify whether a motion is recognized based on the first motion sensor signal. For example, in the case of exercise in which a movement of the arm is small or insignificant according to the exercise item, a motion may not be recognized in the first electronic device 210 worn on the wrist.

According to various embodiments, when the motion is not recognized based on the first motion sensor signal, the processor 211 or 231 may receive a second motion sensor signal obtained by driving the motion sensor 227 of the second electronic device 220 in operation 509.

According to various embodiments, in operation 511, the processor 211 or 231 may identify whether a motion is recognized based on the second motion sensor signal received from the motion sensor 227. For example, when a motion by the first motion sensor signal is not recognized due to a fixed movement of the arm part in the first electronic device 210 worn on the wrist, the motion may be recognized by the second motion sensor signal obtained from the second electronic device 220 according to an action of moving a torso.

According to various embodiments, when the motion is not recognized based on the second motion sensor signal, the processor 211 or 231 may identify whether the first electronic device 210 or the third electronic device 230 may perform an UWB ranging function with the second electronic device 220 or whether a sensor signal may be recognized by the barometric pressure sensor 226 of the second electronic device 220 in operation 513. For example, when the user moves very slowly or stops exercise because it is hard while performing an exercise item such as a push-up, the motion by the second motion sensor signal may not be recognized.

According to various embodiments, if the processor 211 or 231 may recognize UWB ranging or the barometric pressure sensor 226, the processor 211 or 231 may perform UWB ranging between the first electronic device 210 or the third electronic device 230 and the second electronic device 220 to obtain information on a change in a distance value or may drive the barometric pressure sensor 226 of the second electronic device 220 to obtain information on a change in a height value in operation 515.

According to various embodiments, in operation 517, the processor 211 or 231 may provide workout data such as the number of exercise, an exercise time, an exercise speed, or exercise calories based on a first motion sensor signal, a second motion sensor signal, information on a change in a distance value according to UWB ranging, or information on a change in a height value by the barometric pressure sensor 226.

According to an embodiment, the processor 211 or 231 may count the number of exercises based on a change point of data obtained by processing the first motion sensor signal or the second motion sensor signal. For example, the processor 211 or 231 may detect a point at which a data value changes from a positive value to a negative value or vice versa based on 0, and count an interval between one change point and the next change point as one exercise period.

According to an embodiment, the processor 211 or 231 may count the number of exercises based on change information on a distance value according to UWB ranging or change information on a height value by the barometric pressure sensor 226. For example, the processor 211 or 231 may detect a point in which a change value changes from a positive value to a negative value or vice versa based on 0, or a point in which a distance value or a height value changes from an increase to a decrease or vice versa and count an interval between one change point and the next change point as one exercise period.

Figure 6:
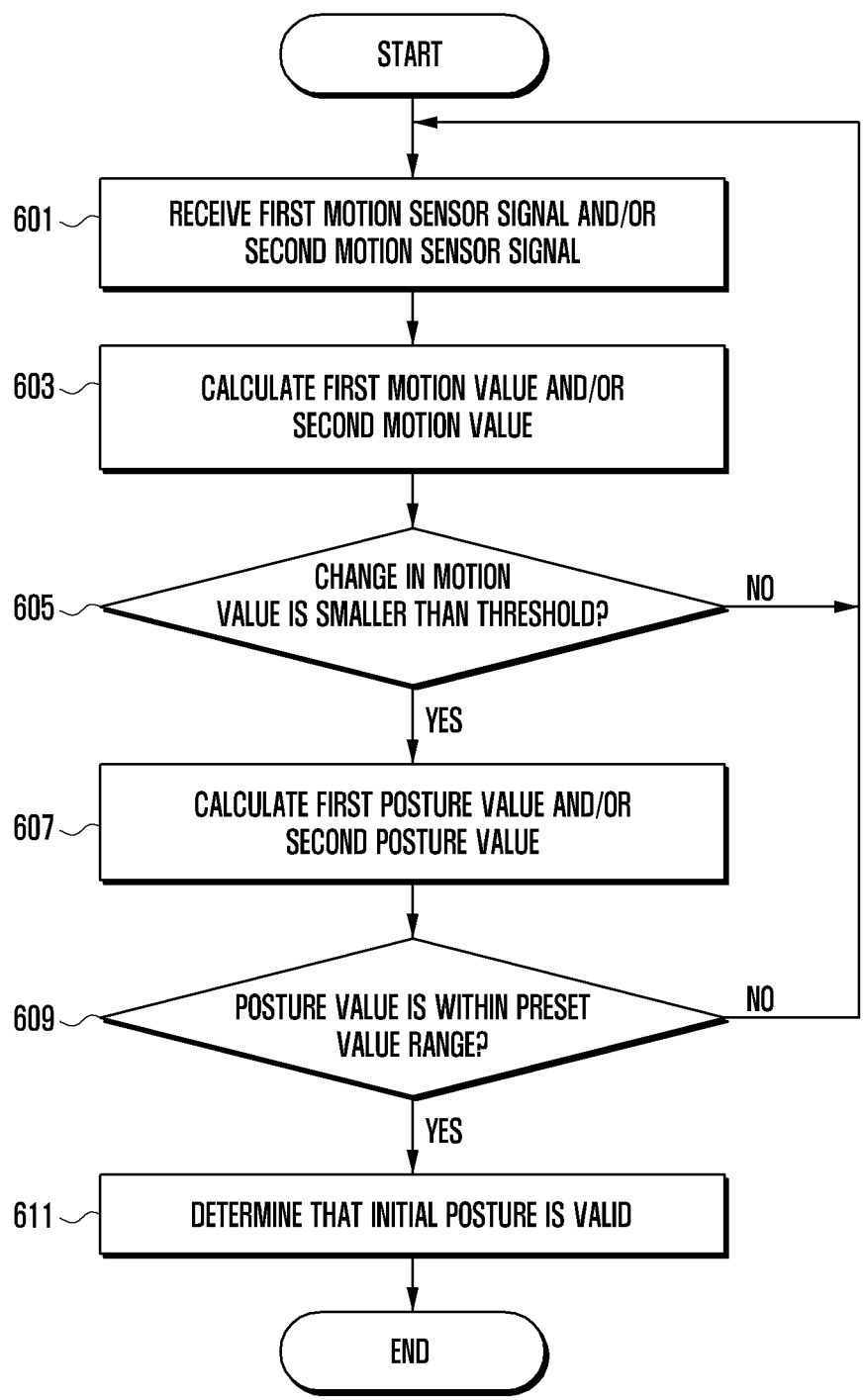
FIG. 6 is a flowchart illustrating an operation of determining initial posture validity according to an embodiment of the disclosure.

FIG. 6 is a flowchart illustrating an operation of determining initial posture validity according to an embodiment of the disclosure.

Referring to FIG. 6, the processor (e.g., the processor 211 or 231 of FIG. 2) of the first electronic device (e.g., the first electronic device 210 of FIG. 2) or the third electronic device (e.g., the third electronic device 230 of FIG. 2) may determine the validity of an initial exercise posture based on a motion sensor signal obtained from the sensor module (e.g., the motion sensor 217 or 227 of FIG. 2) of the first electronic device 210 or the second electronic device (e.g., the second electronic device 220 of FIG. 2).

According to an embodiment, the first electronic device 210 may directly connect with the second electronic device 220 through the third communication link 203 with various communication methods such as Bluetooth to transmit and receive a signal. According to another embodiment, the third electronic device 230 may connect with the first electronic device 210 and the second electronic device 220 through the first communication link 201 and the second communication link 202 with various communication methods such as Bluetooth to transmit and receive a signal.

According to various embodiments, the processor 211 or 231 may determine the validity of an initial posture based on whether a movement is stopped for a predetermined time and a designated posture value is maintained.

According to various embodiments, in operation 601, the processor 211 or 231 may receive a first motion sensor signal obtained from the motion sensor 217 and/or a second motion sensor signal obtained from the motion sensor 227.

According to an embodiment, the first motion sensor signal may be acceleration sensor data and/or gyro sensor data obtained from the acceleration sensor 218 and/or the gyro sensor 219 of the motion sensor 217. According to an embodiment, the second motion sensor signal may be acceleration sensor data and/or gyro sensor data obtained from the acceleration sensor 228 and/or the gyro sensor 229 of the motion sensor 227.

According to an embodiment, the processor 211 or 231 may receive a plurality of first motion sensor signals obtained by driving the motion sensor 217 for a specified time and/or a plurality of second motion sensor signals obtained by driving the motion sensor 227.

According to various embodiments, in operation 603, the processor 211 or 231 may calculate a first motion value and/or a second motion value based on the first motion sensor signal and/or the second motion sensor signal.

According to an embodiment, the first motion value or the second motion value may be a value indicating a magnitude of a movement calculated based on the first motion sensor signal or the second motion sensor signal, respectively. For example, the first motion value or the second motion value $a_{NORM}$ may be calculated as an acceleration 3-axis absolute value (magnitude), as illustrated in Equation 1.

$$a_{NORM} = \sqrt{x^2 + y^2 + z^2} \qquad \text{Equation 1}$$

According to an embodiment, in operation 605, the processor 211 or 231 may determine whether an amount of change in the motion value is smaller than a specified threshold value.

According to an embodiment, the processor 211 or 231 may compare an amount of change in a motion value calculated based on a motion sensor signal received for a predetermined time with a specified threshold value. According to an embodiment, the processor 211 or 231 may compare an amount of change in a first motion value calculated based on a first motion sensor signal received for a predetermined time with a specified threshold value. According to an embodiment, the processor 211 or 231 may compare an amount of change in a second motion value calculated based on a second motion sensor signal received for a predetermined time with a specified threshold value. For example, the amount of change (diff_sum(k)) of the motion value for a predetermined time may be calculated based on Equation 2.

$$\text{diff sum}(k) = \sum_{i=k-N+1}^{k} \{a_{NORM}(i) - a_{NORM}(i-1)\} \qquad \text{Equation 2}$$

According to an embodiment, a valid initial posture may include a state in which the user stops a movement for a predetermined time and takes an initial setup posture for starting exercise. As described above, when an amount of change in the motion value calculated based on a motion sensor signal received for a predetermined time is smaller than a specified threshold value, it may be determined that a movement is in a stopped state. For example, each of amounts of change in a first motion value or a second motion value indicating a movement of each of the first electronic device 210 worn on the wrist and the second electronic device 220 worn on the ear in a state in which a movement of the user's arm and head is stopped and fixed may be smaller than a specified threshold value.

According to an embodiment, when the amount of change in the motion value is greater than or equal to a specified threshold value, it may be determined that the user is in a moving state and does not take a valid initial posture. According to an embodiment, the processor 211 or 231 may provide a notification for inducing the user to take a valid initial posture through the touch screen (e.g., the touch screen 214 or 234 of FIG. 2).

According to various embodiments, in operation 607, the processor 211 or 231 may calculate a first posture value and/or a second posture value based on the first motion sensor signal and/or the second motion sensor signal, in operation 609, the processor 211 or 231 may identify whether each of the first posture value and/or the second posture value is within a configuration value range, and when the posture value is within a configuration value range, the processor 211 or 231 may determine that the initial posture is valid in operation 611.

According to an embodiment, the processor 211 or 231 may determine the validity of the initial posture based on whether a movement is stopped for a predetermined time and the configured posture value is maintained. For example, in the case of push-up exercise, a posture facing the ground with a hand on the floor and a body facing down may be taken as an initial posture, and the processor 211 or 231 may identify whether a first posture value measured by placing the hand on the floor in a movement stop state based on a first motion sensor signal from the first electronic device 210 worn on the wrist falls a range within the threshold value from a specified configuration value, and identify whether a second posture value measured by viewing the ground in a movement stop state based on a second motion sensor signal from the second electronic device 220 worn on the ear falls a range within a threshold value from a specified preset value.

Figure 7:
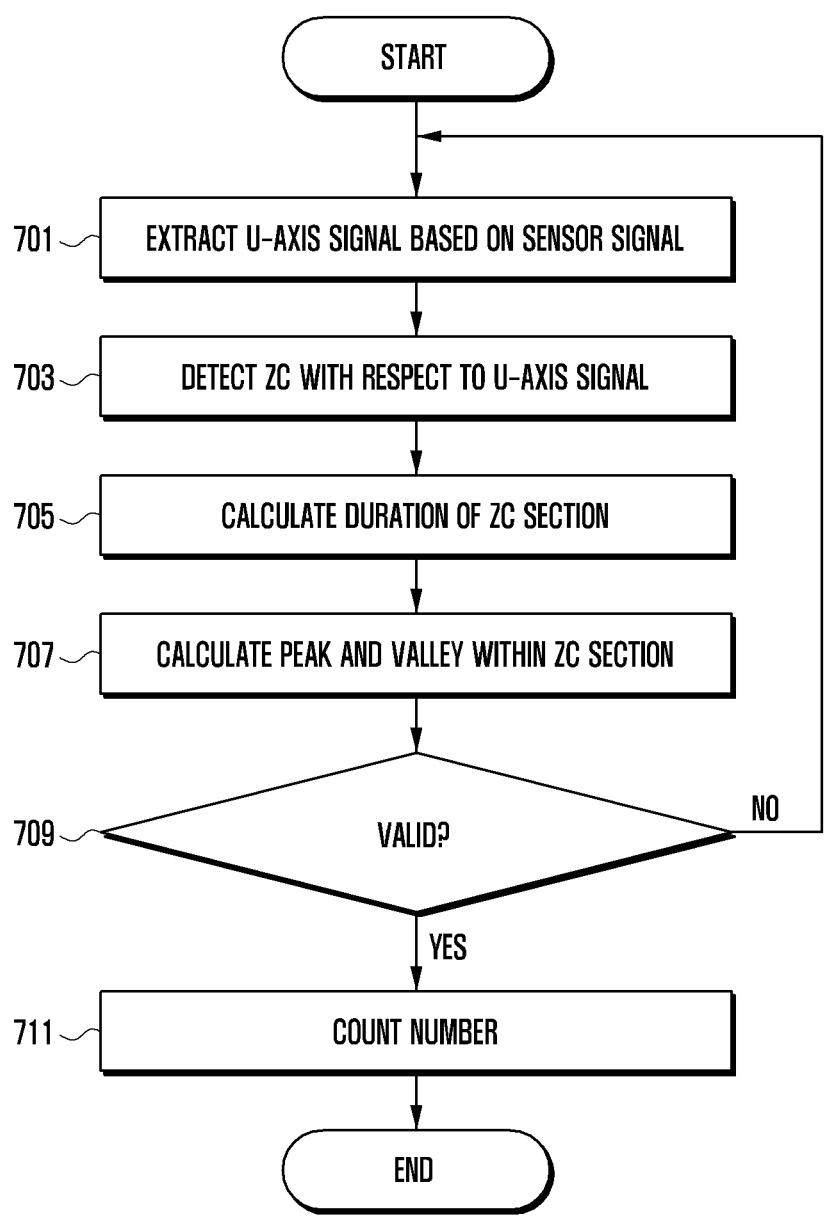
FIG. 7 is a flowchart illustrating an operation of obtaining workout data according to an embodiment of the disclosure.

FIG. 7 is a flowchart illustrating an operation of obtaining workout data according to an embodiment of the disclosure.

Referring to FIG. 7, the processor (e.g., the processor 211 or 231 of FIG. 2) of the first electronic device (e.g., the first electronic device 210 of FIG. 2) or the third electronic device (e.g., the third electronic device 230 of FIG. 2) may obtain workout data based on a motion sensor signal obtained from the sensor module (e.g., the motion sensor 217 or 227 of FIG. 2) of the first electronic device 210 or the second electronic device (e.g., the second electronic device 220 of FIG. 2).

According to an embodiment, the first electronic device 210 may directly connect with the second electronic device 220 through the third communication link 203 with various communication methods such as Bluetooth to transmit and receive a signal. According to another embodiment, the third electronic device 230 may connect with the first electronic device 210 through the first communication link 201 with various communication methods such as Bluetooth to transmit and receive a signal or may be connected to the second electronic device 220 through the second communication link 202 to transmit and receive a signal.

According to various embodiments, in operation 701, the processor 211 or 231 may extract a U-axis signal component based on a motion sensor signal obtained by the motion sensor 217 of the first electronic device 210 or a motion sensor signal obtained by the motion sensor 227 of the second electronic device 220.

According to an embodiment, the motion sensor signal obtained by the motion sensor 217 of the first electronic device 210 or the motion sensor 227 of the second electronic device 220 is data about coordinates of a body frame of the first electronic device 210 or the second electronic device 220 and may be converted into coordinates based on an E-axis, an N-axis, and an U-axis of a navigation frame (east north up (ENU)), and a U-axis signal component may be extracted therefrom. Exercise items performed by the user, such as a push-up, a pull-up, or an inverted row, mainly include items performed while moving up and down based on the ground against gravity, and more accurate movement data may be extracted by using U-axis data that may represent a ground-based vertical movement by converting a body frame coordinate axis of the first electronic device 210 or the second electronic device 220 into a navigation frame coordinate axis.

According to various embodiments, the processor 211 or 231 may detect a zero crossing (ZC) section with respect to the U-axis signal component in operation 703. According to an embodiment, the processor 211 or 231 may detect a point at which the U-axis signal component value increases from (−) to (+) or decreases from (+) to (−) based on a value of 0, a section between consecutive zero-crossing points, for example, may detect from a previous zero-crossing point to a current zero-crossing point as one zero-crossing section. For example, when the processor 211 or 231 detects a point at which the U-axis signal component value decreases from (+) to (−) as a zero crossing point, the processor 211 or 231 may detect a section from the previous decrease point to the current decrease point as one zero-crossing section.

According to various embodiments, the processor 211 or 231 may calculate the duration of a zero crossing (ZC) section detected for the U-axis signal component in operation 705, and calculate a peak and a valley of the U-axis signal component within the zero crossing section in operation 707.

According to various embodiments, in operation 709, the processor 211 or 231 may identify whether a length, a peak, and/or a valley of the calculated zero-crossing section is valid. According to an embodiment, the processor 211 or 231 may identify whether the length of the zero-crossing section is within a range greater than or equal to the specified minimum length and less than or equal to the maximum length, and whether each of a peak and/or a valley of the U-axis signal component exists within a range greater than or equal to a specified valley and less than or equal to a maximum value.

According to various embodiments, when the length, the peak, and/or the valley of the zero-crossing section are valid, the processor 211 or 231 may count the corresponding zero-crossing section as the number of valid one exercise in operation 711. According to an embodiment, the processor 211 or 231 may obtain various workout data such as the number of exercises, an exercise time, exercise intensity, and/or consumed calories according to the count of the number of valid one exercise according to the calculation of the length, the peak, and/or the valley of the zero-crossing section.

Figure 8:
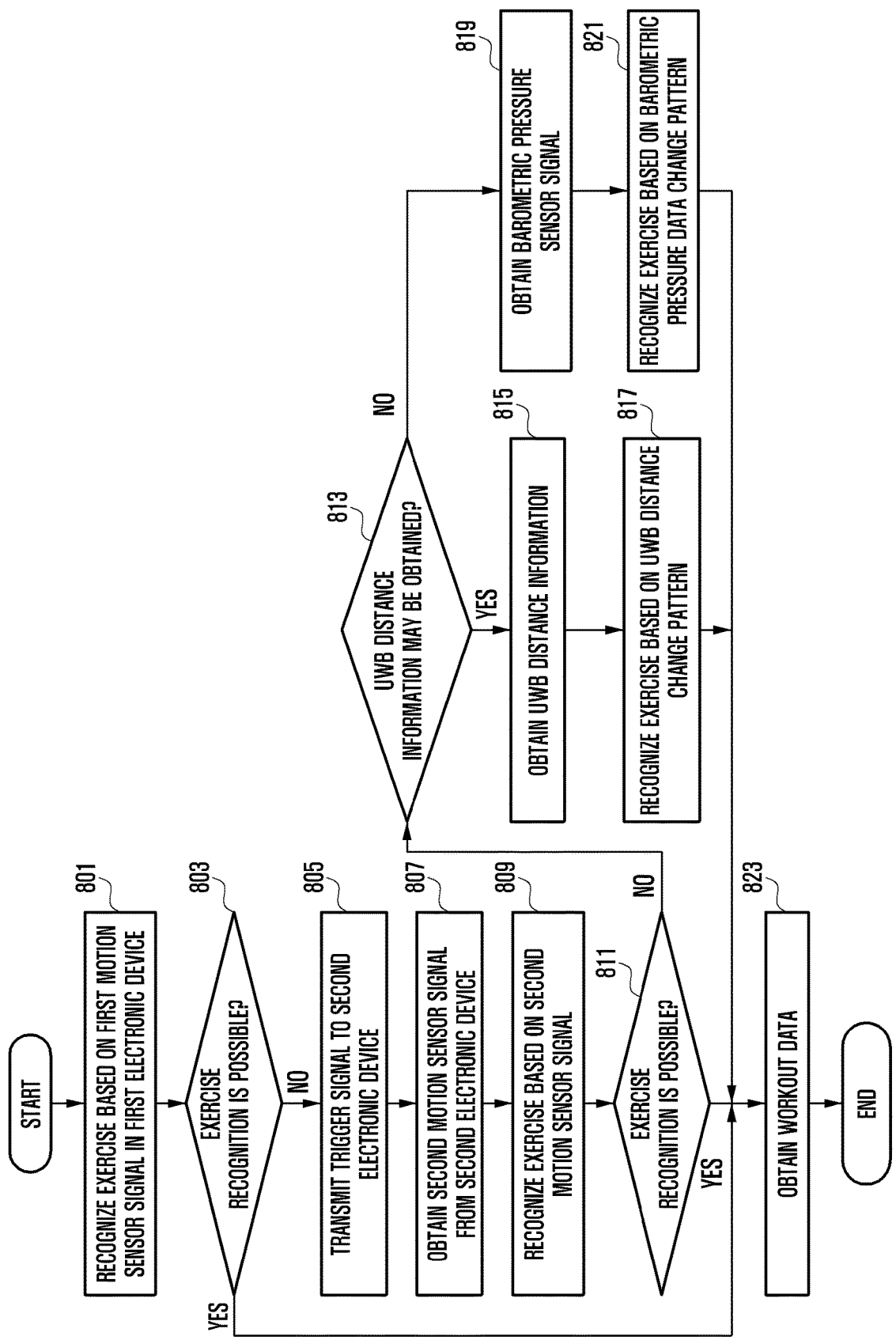
FIG. 8 is a flowchart illustrating an operation of obtaining workout data by controlling a plurality of electronic devices according to an embodiment of the disclosure.

FIG. 8 is a flowchart illustrating an operation of obtaining workout data by controlling a plurality of electronic devices according to an embodiment of the disclosure.

Figure 9A:
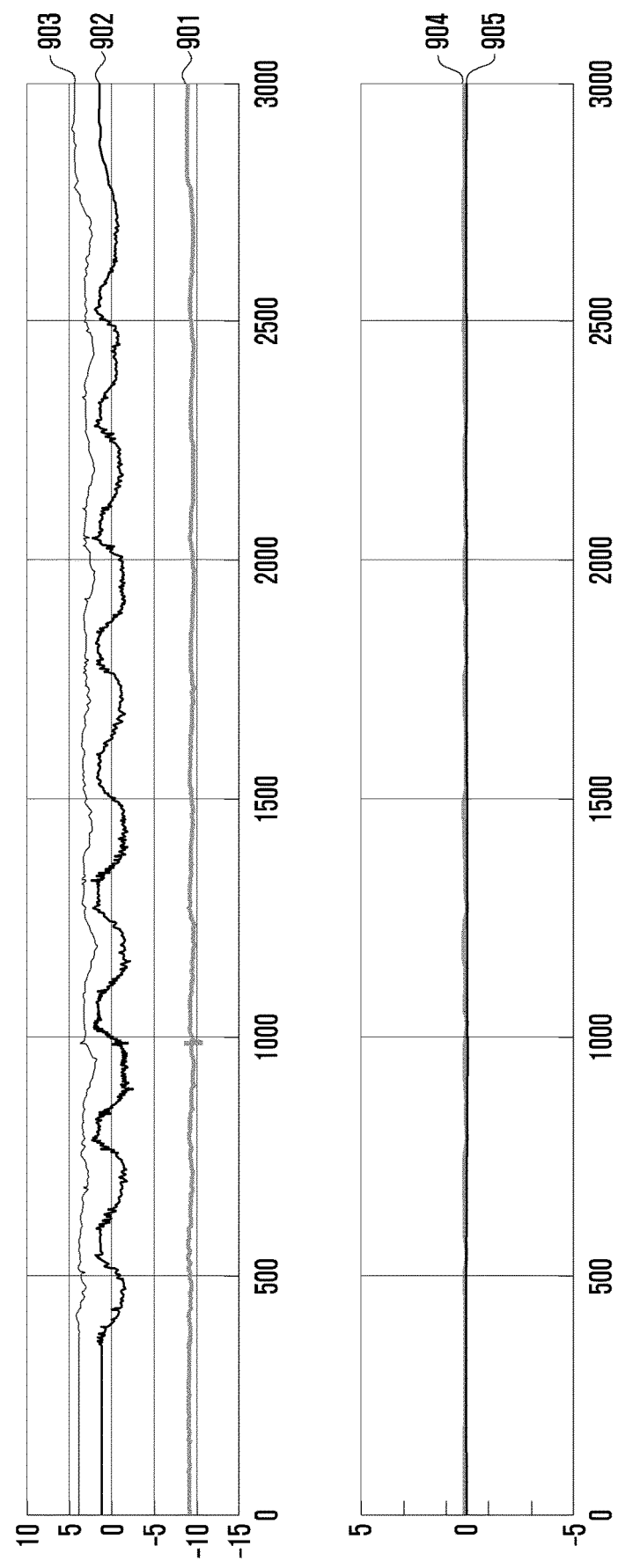
FIGS. 9A, 9B, and 9C are diagrams illustrating an operation of obtaining workout data from various sensor signals according to various embodiments of the disclosure.
Figure 9B:
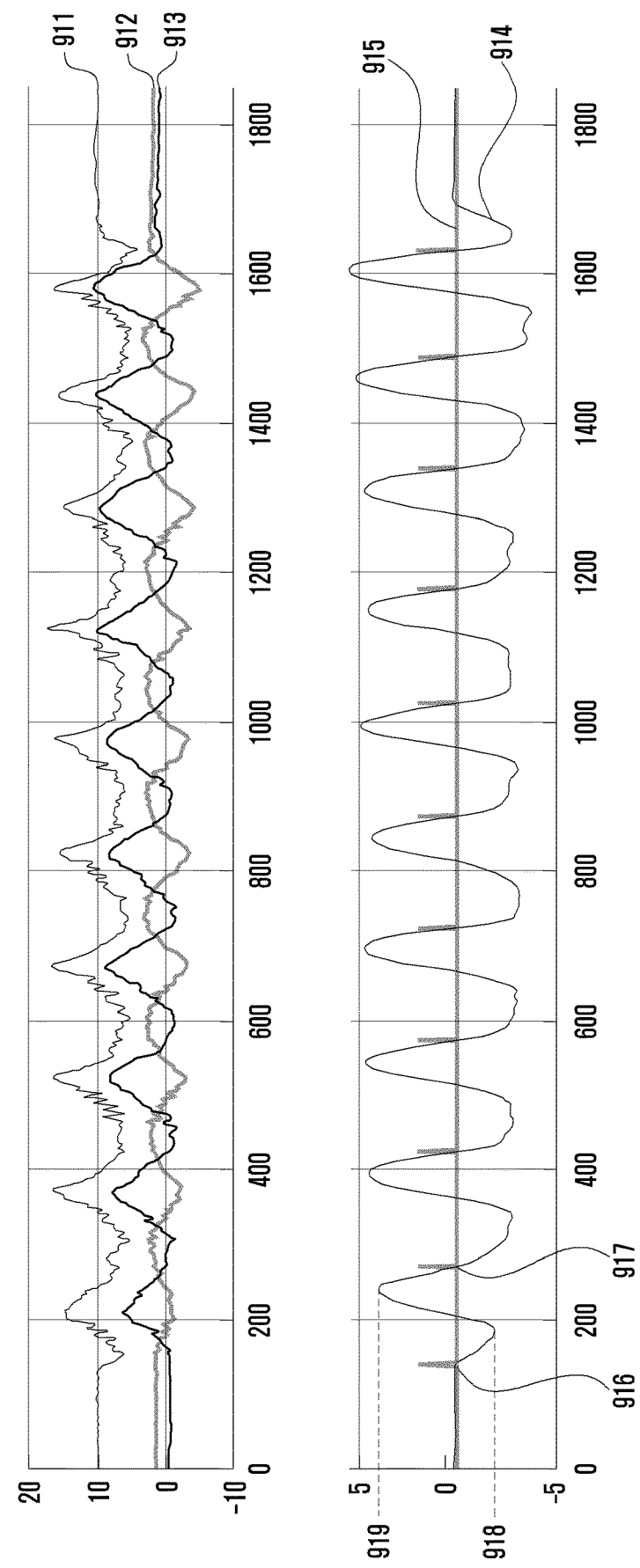
Figure 9C:
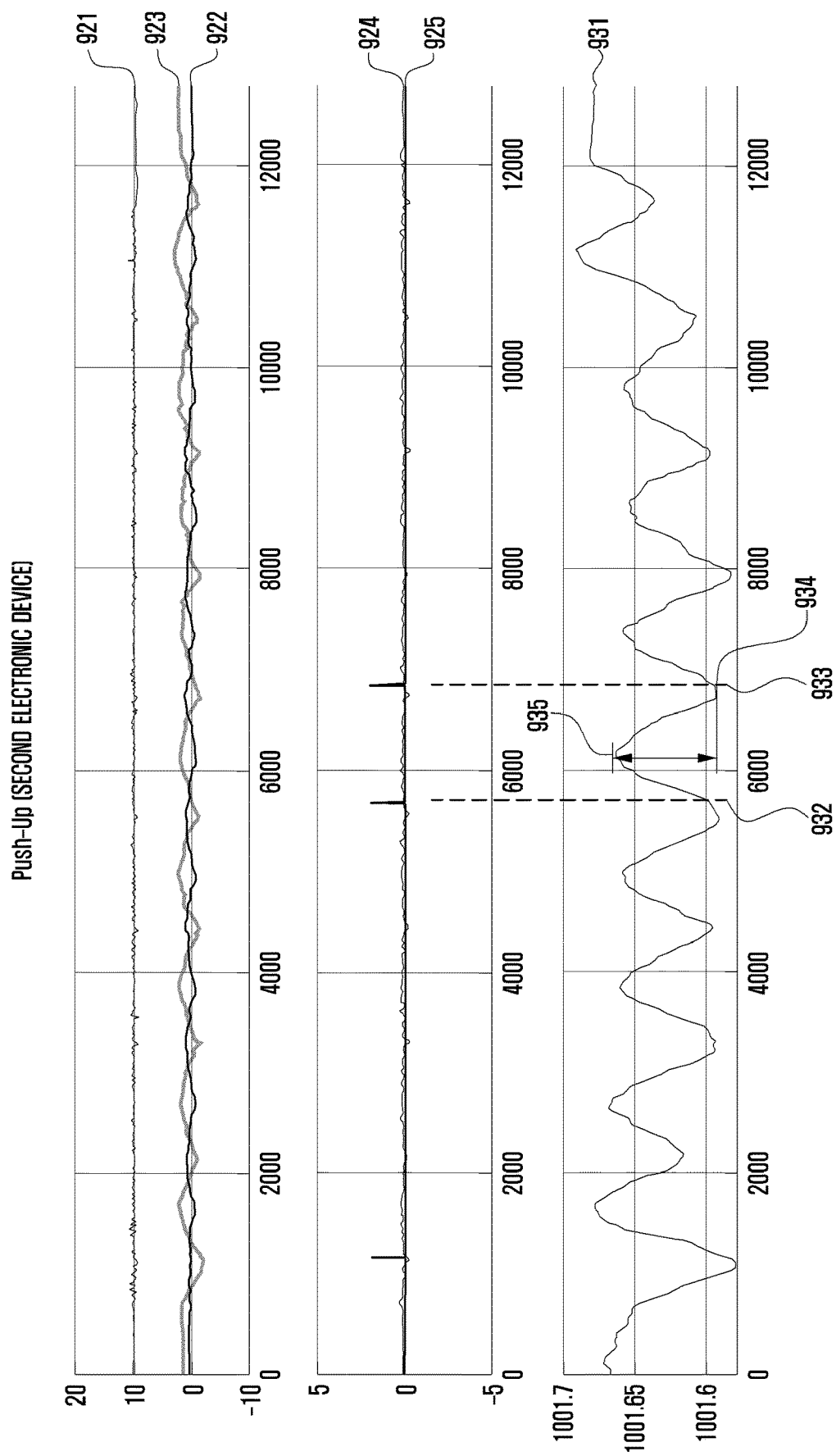

FIGS. 9A, 9B and 9C are diagrams illustrating an operation of obtaining workout data from various sensor signals according to various embodiments of the disclosure.

Referring to FIG. 8, the processor (e.g., the processor 211 or 231 of FIG. 2) of the first electronic device (e.g., the first electronic device 210 of FIG. 2) or the third electronic device (e.g., the third electronic device 230 of FIG. 2) may calculate workout data based on a motion sensor signal obtained from the acceleration sensor (e.g., the acceleration sensor 218 or 228 of FIG. 2) and/or the gyro sensor (e.g., the gyro sensor 219 or 229 of FIG. 2) of the motion sensor (e.g., the motion sensor 217 or 227 of FIG. 2) of the first electronic device 210 or the second electronic device (e.g., the second electronic device 220 of FIG. 2).

According to an embodiment, the processor 211 or 231 of the first electronic device 210 or the third electronic device 230 may calculate workout data based on the motion sensor signal obtained from the acceleration sensor 218 or 228 and/or the gyro sensor 219 or 229 of the motion sensor 217 or 227.

According to an embodiment, when the processor 211 or 231 of the first electronic device 210 or the third electronic device 230 cannot calculate workout data based on the above-described motion sensor signal, the processor 211 or 231 may calculate workout data based on distance change information according to UWB ranging between the second electronic device 220 and the third electronic device 230 or based on a sensor signal of the barometric pressure sensor (e.g., the barometric pressure sensor 226 of FIG. 2) of the second electronic device 220.

According to an embodiment, the first electronic device 210 may directly connect with the second electronic device 220 through the third communication link 203 with various communication methods such as Bluetooth to transmit and receive a signal. According to another embodiment, the third electronic device 230 may connect with the first electronic device 210 and the second electronic device 220 through the first communication link 201 and the second communication link 202 with various communication methods such as Bluetooth to transmit and receive a signal.

According to various embodiments, in operation 801, the processor 211 or 231 may perform exercise recognition based on a first motion sensor signal obtained from the motion sensor 217 of the first electronic device 210.

According to an embodiment, the processor 211 or 231 may perform coordinate transformation of the first motion sensor signal obtained from the motion sensor 217 of the first electronic device 210 into, for example, a navigation frame, extract a U-axis signal component, detect a zero-crossing section, and count the number of exercises, thereby performing exercise recognition.

According to an embodiment, in operation 803, the processor 211 or 231 may determine whether exercise recognition is possible based on the first motion sensor signal, and if exercise recognition is not possible, the processor 211 or 231 may transmit a signal triggering acquisition of the second motion sensor signal to the second electronic device 220 by the motion sensor 227 in operation 805.

Referring to FIG. 9A, it illustrates an example of a signal processing result of a first motion sensor signal, for example, an acceleration sensor signal obtained by the first electronic device 210 when push-up exercise is performed 10 times. With reference to the drawing, an upper graph representing a three-axis signal of a body frame of the acceleration sensor signal represents an x-axis signal component 901, a y-axis signal component 902, and a z-axis signal component 903, and a lower graph represents an U-axis signal 904 extracted after performing coordinate transformation of the three-axis signal of the upper body frame into a navigation frame. Because it is difficult to detect zero crossing 905 from the U-axis signal of the acceleration sensor signal obtained from the first electronic device 210 worn on the wrist while performing push-up exercise having a characteristic in which the hand is fixed during the exercise, it can be seen that exercise recognition is impossible.

According to various embodiments, the processor 211 or 231 may obtain a second motion sensor signal from the second electronic device 220 in operation 807, and perform exercise recognition based on the second motion sensor signal in operation 809.

According to an embodiment, the processor 211 or 231 may perform coordinate transformation of the second motion sensor signal obtained from the motion sensor 227 of the second electronic device 220 into, for example, a navigation frame, extract a U-axis signal component, detect a zero-crossing section, and count the number of exercises, thereby performing exercise recognition.

According to various embodiments, in operation 811, the processor 211 or 231 may identify whether exercise recognition is possible based on the second motion sensor signal, and if exercise recognition is possible, the processor 211 or 231 may obtain workout data in operation 823.

Referring to FIG. 9B, it illustrates an example of a signal processing result of a second motion sensor signal, for example, an acceleration sensor signal obtained by the second electronic device 220 when push-up exercise is performed 10 times. With reference to the drawing, an upper graph representing a three-axis signal of a body frame of an acceleration sensor signal represents an x-axis signal component 911, an y-axis signal component 912, and a z-axis signal component 913, and a lower graph represents an U-axis signal 914 extracted after performing coordinate transformation of the three-axis signal of the upper body frame into a navigation frame. Zero crossing 915 may be detected from a U-axis signal of an acceleration sensor signal obtained from the second electronic device 220 worn on the ear while performing push-up exercise having a characteristic that a body including a head moves up and down during the exercise, and for example, a section between a previous zero-crossing point 916 and a current zero-crossing point 917 may be counted as a one exercise execution section, and in the one exercise execution section, a valley 918 and a peak 919 may be detected as workout data.

According to an embodiment, while the user loses strength, for example, due to fatigue accumulation upon performing exercise, and when an exercise speed slows down, extraction of the U-axis signal based on a motion sensor signal obtained through the motion sensor 217 or 227 and accordingly exercise recognition may become impossible.

According to various embodiments, when the processor 211 or 231 is unable to recognize exercise based on the second motion sensor signal, the processor 211 or 231 may identify whether distance information may be obtained according to UWB ranging between the first electronic device 210 and the second electronic device 220 in operation 813.

According to an embodiment, when distance information may be obtained according to UWB ranging between the first electronic device 210 and the second electronic device 220, the processor 211 or 231 may perform UWB ranging between the first electronic device 210 and the second electronic device 220 to obtain UWB distance information in operation 815 and recognize exercise based on a change pattern of the UWB distance in operation 817. For example, the processor 211 or 231 may count a section between a time point at which the distance changes from a previous decrease to an increase and a time point at which the distance changes from a current decrease to an increase as a one exercise execution section from a change pattern of the UWB distance.

According to an embodiment, when distance information may be obtained according to UWB ranging between the first electronic device 210 and the second electronic device 220, the processor 211 or 231 may enable to perform UWB ranging between the first electronic device 210 and the second electronic devices 220 to obtain UWB distance information in operation 815, recognize exercise based on a change pattern of the UWB distance in operation 817, and obtain workout data based on this in operation 823. For example, the processor 211 or 231 may extract a time point at which the distance changes from a previous decrease to an increase and a time point at which the distance changes from a current decrease to an increase, and count a section between these time points as one time exercise execution section from the change pattern of the UWB distance.

According to an embodiment, when it is impossible to obtain distance information according to UWB ranging between the first electronic device 210 and the second electronic device 220, the processor 211 or 231 may enable to obtain barometric pressure sensor data from the barometric pressure sensor 226 of the second electronic device 220 in operation 819, analyze the barometric pressure sensor data to recognize exercise through a periodic change pattern in operation 821, and for example, extract a time point in which data changes from a previous decrease to an increase and a time point in which data changes from a current decrease to an increase from the change pattern of the barometric pressure sensor data, and count a section between these time points as a one exercise execution section in operation 823.

Referring to FIG. 9C, the upper graph illustrates an example of a signal processing result of a second motion sensor signal, for example, an acceleration sensor signal obtained by the second electronic device 220 when push-up exercise is performed 10 times. With reference to the drawing, an upper graph representing a three-axis signal of a body frame of the acceleration sensor signal represents an x-axis signal component 921, an y-axis signal component 922, and a z-axis signal component 923, and a middle graph represents an U-axis signal 924 extracted after performing coordinate transformation of the three-axis signal of the upper body frame into the navigation frame. During exercise, because it is difficult to detect zero crossing 925 from the U-axis signal of the acceleration sensor signal obtained from the second electronic device 220 worn on the ear for various reasons, exercise recognition may become impossible. A lower graph is a graph representing a barometric pressure sensor signal value 931 of the barometric pressure sensor 226 of the second electronic device 220, and it can be seen that the barometric pressure sensor signal 931 represents a periodic signal pattern. The processor 211 or 231 may extract, for example, a time point 932 changing from a previous decrease to an increase and a time point 933 changing from a current decrease to an increase from the change pattern of the barometric pressure sensor signal 931, count a section between these time points as a one exercise execution section, and extract a valley 934 and a peak 935 as workout data.

Figure 10:
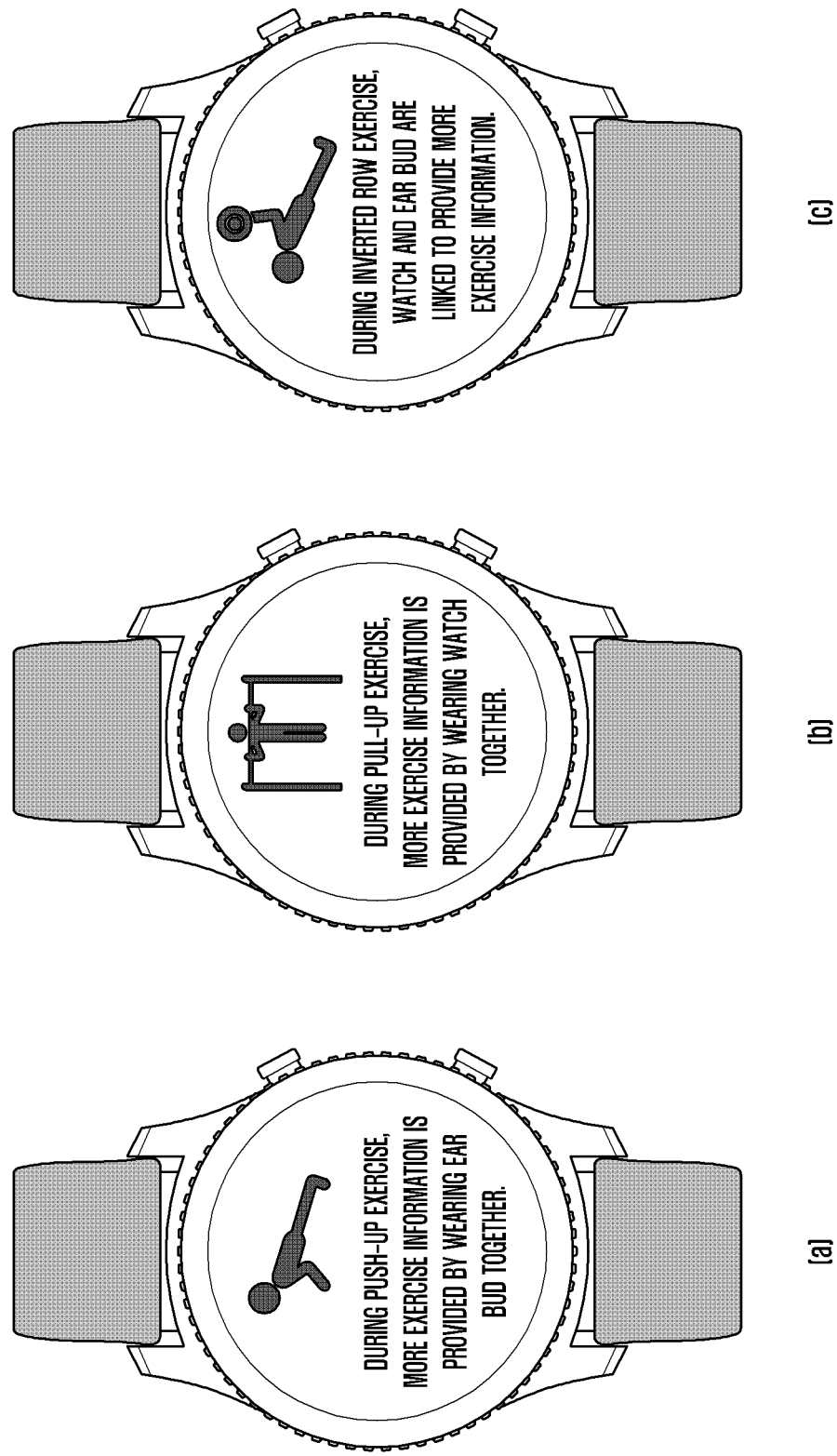
FIG. 10 is a diagram illustrating examples of a user interface that provides a guide for obtaining workout data according to an embodiment of the disclosure.

FIG. 10 is a diagram illustrating examples of a user interface that provides a guide for obtaining workout data according to an embodiment of the disclosure.

According to an embodiment, as in an exercise item in which a torso moves against gravity in a state in which a hand is fixed, such as a push-up, a pull-up, or an inverted row, in the case of an exercise item in which it is difficult to obtain workout data with one device (e.g., the first electronic device 210 of FIG. 2), a guide suggesting to wear together another device (e.g., the second electronic device 220 of FIG. 2) and to start measuring the exercise may be displayed on the touch screen (e.g., the touch screen 214 of FIG. 1) of the first electronic device 210.

Referring to part (a), (b), or (c) of FIG. 10, for example, a push-up, pull-up, or inverted row exercise item may display a guide including an image and/or text for the respective exercise along with a guide phrase suggesting to wear together the second electronic device 220.

FIG. 10 illustrates an example of displaying the guide on the touch screen 214 of the first electronic device 210, but this embodiment is not limited thereto, and for example, a guide may be provided through the touch screen 234 of the third electronic device 230 of FIG. 2.

Figure 11:
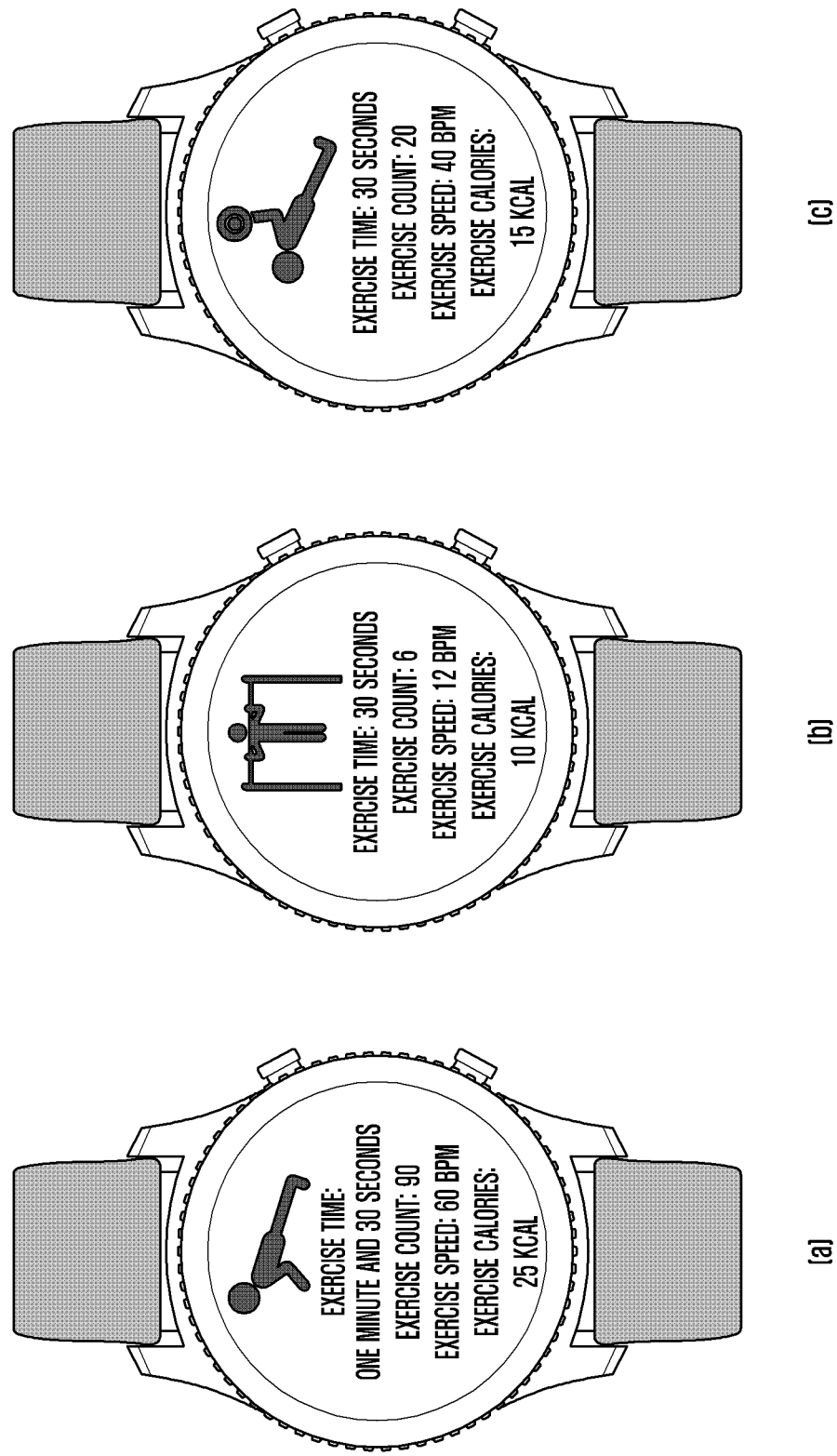
FIG. 11 is a diagram illustrating examples of a user interface that provides workout data according to various exercise items according to an embodiment of the disclosure.

FIG. 11 is a diagram illustrating examples of a user interface that provides workout data exercise items according to an embodiment of the disclosure.

According to an embodiment, as in an exercise item in which a torso moves against gravity in a state in which a hand is fixed, such as a push-up, a pull-up, or an inverted row, in the case of an exercise item in which it is difficult to obtain workout data with one device (e.g., the first electronic device 210 of FIG. 2), as workout data is obtained by wearing together another device (e.g., the second electronic device 220 of FIG. 2) and starting exercise measurement, workout data may be displayed on a touch screen (e.g., the touch screen 214 of FIG. 1) of the first electronic device 210.

Referring to part (a), (b), or (c) of FIG. 11, for example, a push-up, pull-up, or inverted row exercise item may display workout data including an image and/or a text for the respective exercise. For example, the workout data may include an exercise time, the number of exercises, an exercise speed, or exercise calories.

FIG. 11 illustrates an example of displaying the guide on the touch screen 214 of the first electronic device 210, but this embodiment is not limited thereto and for example, a guide may be provided through the touch screen 234 of the third electronic device 230 of FIG. 2.

Figure 12:
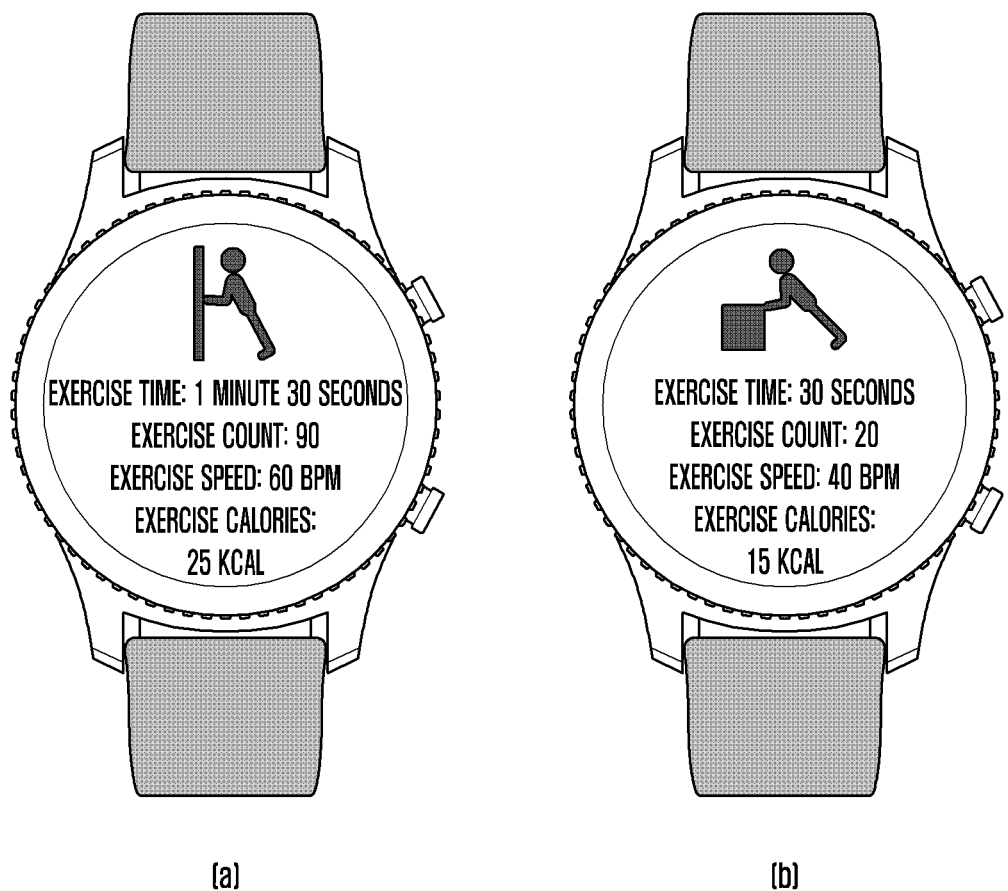
FIG. 12 is a diagram illustrating examples of a user interface that provides workout data exercise items according to an embodiment of the disclosure.

FIG. 12 is a diagram illustrating examples of a user interface that provides workout data according to various exercise items according to an embodiment of the disclosure.

According to an embodiment, in the case of exercise in which a torso moves obliquely or horizontally instead of up and down in a state in which a hand is fixed, such as a wall pushup and an incline pushup, unlike the examples of FIG. 11, exercise recognition based on the motion sensor signal may be somewhat unstable. In this case, exercise is recognized by the motion sensor signal, but as described above, workout data may be obtained through measurement of a distance between the first electronic device 210 and the second electronic device 220 through UWB ranging and additional exercise recognition based thereon.

According to an embodiment, as in exercise item in which one body part is fixed and another body part is moved, in the case of exercise items in which it is difficult to obtain workout data with one device (e.g., the first electronic device 210 of FIG. 2), another device (e.g., the second electronic device 220 of FIG. 2) may be worn together, exercise may be recognized and workout data may be obtained through UWB ranging as well as a motion sensor signal, and workout data may be displayed on the touch screen (e.g., the touch screen 214 of FIG. 2) of the first electronic device 210 and/or on the touch screen (e.g., the touch screen 234 of FIG. 2) of the third electronic device 230.

Referring to part (a) or (b) of FIG. 12, for example, a wall push-up or incline push-up exercise item may display workout data including an image and/or a text for the respective exercise. For example, the workout data may include an exercise time, the number of exercises, an exercise speed, or exercise calories.

Figure 13:
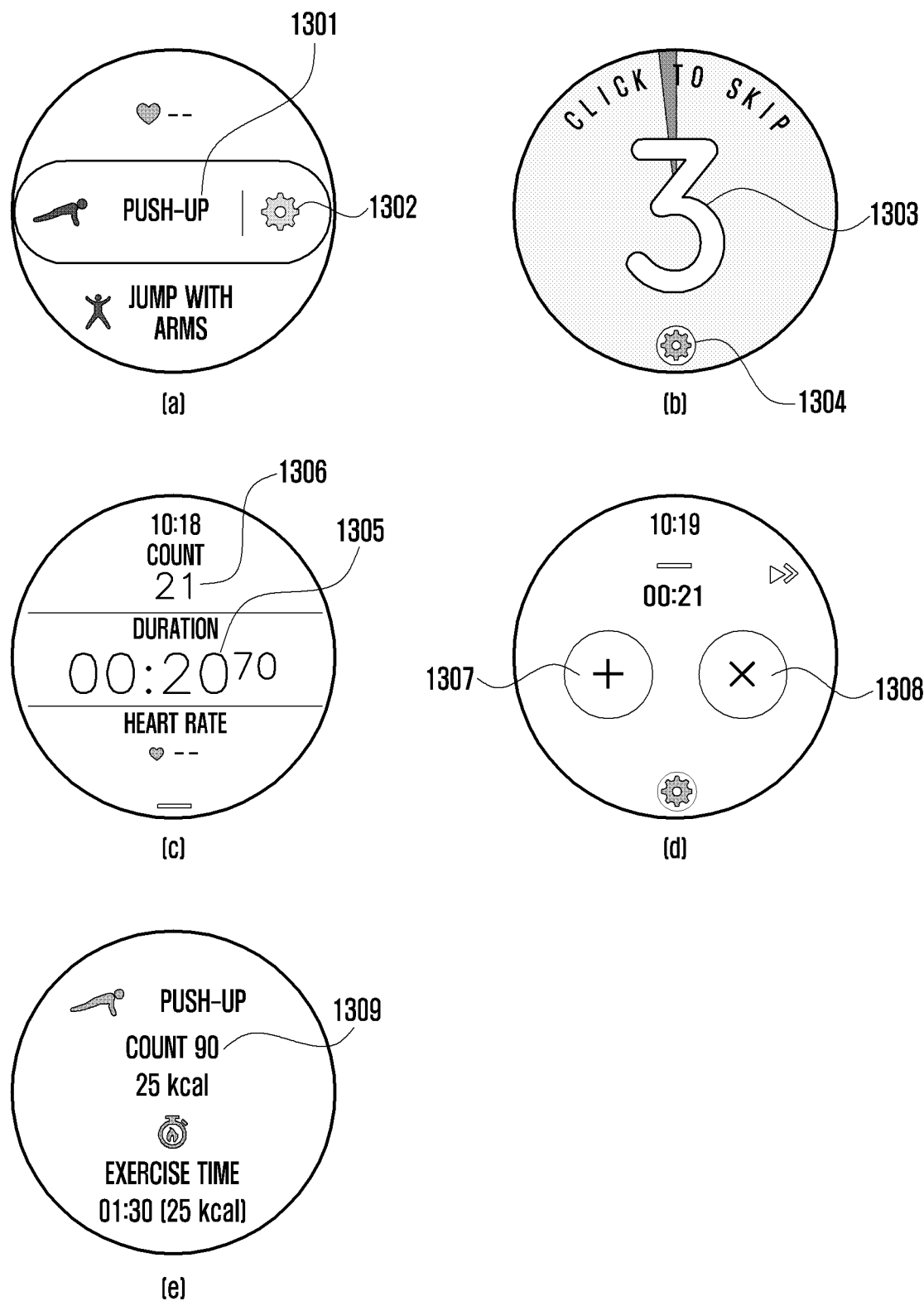
FIG. 13 is a diagram illustrating examples of a user interface that provides workout data according to an exercise item selection according to an embodiment of the disclosure.

FIG. 13 is a diagram illustrating examples of a user interface that provides workout data according to an exercise item selection according to an embodiment of the disclosure.

According to an embodiment, a user may select an exercise item through a touch screen (e.g., the touch screen 214 of FIG. 2) of the first electronic device 210 and/or a touch screen (e.g., the touch screen 234 of FIG. 2) of the third electronic device 230.

Referring to part (a) of FIG. 13, by selecting and touching through, for example, toggling an icon 1301 including a diagram and/or a text (e.g., push-up) indicating an exercise item, a corresponding exercise item may be selected and performed. Further, detailed configurations (e.g., exercise angle) for the corresponding exercise item may be adjusted through a configuration button 1302.

Referring to part (b) of FIG. 13, for example, when the exercise item (e.g., push-up) selected in part (a) of FIG. 13 is touched, a countdown icon 1303 may be displayed so as to start the exercise item, and after a countdown length has elapsed, exercise measurement may be started. Further, detailed configurations (e.g., countdown length) related to countdown may be adjusted through the configuration button 1304. For example, when the countdown icon 1303 is touched, exercise measurement may be immediately started.

Referring to part (c) of FIG. 13, as exercise measurement is started, exercise information such as an exercise time 1305 and/or the number of exercises 1306 may be provided.

According to various embodiments, in the case of exercise items in which it is difficult to obtain workout data with one device (e.g., the first electronic device 210 of FIG. 2), another device (e.g., the second electronic device 220 of FIG. 2) may be worn together, and exercise may be recognized and workout data may be obtained through UWB ranging and/or the barometric pressure sensor 226 of the second electronic device 220 as well as a motion sensor signal.

Referring to part (d) of FIG. 13, when it is identified that a movement has been stopped for a specified time or more through the first electronic device 210 and the second electronic device 220, for example, an icon 1307 for selecting another exercise item and/or an icon 1308 for selecting exercise stop may be provided.

Referring to part (e) of FIG. 13, when the exercise stop icon 1308 is selected in part (d) of FIG. 13, various exercise data 1309 may be displayed on the touch screen 214 of the first electronic device 210 based on the obtained workout data. For example, the workout data may include an exercise time, the number of exercises, or exercise calories.

While the disclosure has been shown and described with reference to various embodiments thereof, it will be understood by those skilled in the art that various changes in form and details may be made therein without departing from the spirit and scope of the disclosure as defined by the appended claims and their equivalents.

The invention claimed is:

1. An electronic device, comprising:
   a display;
   a communication circuit; and
   at least one processor electrically connected to the display and the communication circuit,
   wherein the at least one processor is configured to:
      recognize a user's initial posture based on a motion sensor signal of a first external electronic device received through the communication circuit,
      when the initial posture satisfies a designated condition, control the first external electronic device to transmit, to the electronic device, a first motion sensor signal, and obtain the user's workout data based on the first motion sensor signal,
      when the user's movement is not recognized based on the first motion control signal, control a second external electronic device to transmit, to the electronic device, a second motion sensor signal and obtain the user's workout data based on the second motion sensor signal, and
      display the workout data on at least one of the display or a display included in the first external electronic device.

2. The electronic device of claim 1, wherein the first external electronic device and the second external electronic device are configured to obtain the first motion sensor signal and the second motion sensor signal, respectively according to the user's movement at different positions among the user's body parts.

3. The electronic device of claim 1, wherein the designated condition of the initial posture is determined based on a motion sensor signal of the first external electronic device, and comprises at least one of a condition that the user's movement stops for a specified time or condition that a designated posture value is maintained.

4. The electronic device of claim 1, wherein the processor is configured to control the second external electronic device to transmit, to the electronic device, the second motion sensor signal, when the user's movement is not recognized based on the first motion sensor signal, in that the processor is configured to transmit a trigger signal, requesting to obtain the second motion sensor signal, to the second external electronic device when the user's exercise is not recognized based on the first motion sensor signal.

5. The electronic device of claim 1, wherein the processor is further configured to:
   perform coordinate transformation of the first motion sensor signal or the second motion sensor signal based on an East North Up (ENU) navigation frame,
   extract a U-axis signal component, and
   detect a zero crossing point for the U-axis signal component.

6. The electronic device of claim 5, wherein the processor is further configured to:
   detect a zero-crossing section between consecutive zero-crossing points,
   calculate a peak and a valley within the zero-crossing section, and
   count the zero-crossing section as the number of one exercise when each of the calculated zero crossing section, the peak, and the valley is within a designated range.

7. The electronic device of claim 1, wherein the processor is further configured to:
   identify that both the first external electronic device and the second external electronic device provide an ultra-wide band (UWB) ranging function when the user's movement is not recognized based on the second motion sensor signal,
   control the first external electronic device and the second external electronic device to perform the UWB ranging between the first external electronic device and the second external electronic device to obtain distance information between the first external electronic device and the second external electronic device, and
   obtain the user's workout data based on the distance information between the first external electronic device and the second external electronic device.

8. The electronic device of claim 1, wherein the processor is further configured to:
   control the second external electronic device to transmit, to the electronic device, a barometric pressure sensor signal, and
   obtain the user's workout data based on the barometric pressure sensor signal, when the user's movement is not recognized based on the second motion sensor signal.

9. An electronic device, comprising:
   a display;
   a motion sensor;
   a communication circuit; and
   at least one processor electrically connected to the display, the motion sensor, and the communication circuit,
   wherein the at least one processor is configured to:
      recognize a user's initial posture based on a motion sensor signal received through the motion sensor,
      when the initial posture satisfies a designated condition, control the motion sensor to obtain a first motion sensor signal, and obtain the user's workout data based on the first motion sensor signal, when the user's movement is not recognized based on the first motion sensor signal, control an external electronic device to transmit, to the electronic device, a second motion sensor signal, and obtain the user's workout data based on the second motion sensor signal, and display the workout data on the display.

10. The electronic device of claim 9, wherein the motion sensor and the external electronic device are configured to obtain the first motion sensor signal and the second motion sensor signal, respectively according to the user's movement at different positions among the user's body parts.

11. The electronic device of claim 9, wherein the designated condition of the initial posture is determined based on a motion sensor signal of the motion sensor, and comprises at least one of a condition that the user's movement stops for a specified time or a condition that a designated posture value is maintained.

12. The electronic device of claim 9, wherein the processor is configured to control the external electronic device to transmit, to the electronic device, the second motion sensor signal, and obtain the user's workout data based on the second motion sensor signal, when the user's movement is not recognized based on the first motion sensor signal, in that the processor is further configured to transmit a trigger signal, requesting to obtain the second motion sensor signal, to the external electronic device when the user's exercise is not recognized based on the first motion sensor signal.

13. The electronic device of claim 9, wherein the processor is further configured to:
perform coordinate transformation of the first motion sensor signal or the second motion sensor signal based on an East North Up (ENU) navigation frame,
extract a U-axis signal component, and
detect a zero crossing point for the U-axis signal component.

14. The electronic device of claim 13, wherein the processor is further configured to:
detect a zero-crossing section between consecutive zero-crossing points,
calculate a peak and a valley within the zero-crossing section, and
count the zero-crossing section as the number of one exercise when each of the calculated zero crossing section, the peak, and the valley is within a designated range.

15. The electronic device of claim 9, wherein, when the user's movement is not recognized based on the second motion sensor signal, the processor is further configured to:
identify that the external electronic device supports an ultra-wide band (UWB) ranging through the communication circuit,
perform UWB ranging with the external electronic device through the communication circuit to obtain distance information between the electronic device and the external electronic device when the external electronic device provides an UWB ranging function, and
obtain user's workout data based on the distance information between the electronic device and the external electronic device.

16. The electronic device of claim 9, wherein, when the user's movement is not recognized based on the second motion sensor signal, the processor is further configured to:
control the external electronic device to transmit, to the electronic device, a barometric pressure sensor signal, and
obtain the user's workout data based on the barometric pressure sensor signal.

17. A method of operating an electronic device, the method comprising:
recognizing a user's initial posture based on a motion sensor signal obtained from a first external electronic device;
obtaining, when the initial posture satisfies a designated condition, the user's workout data based on a first motion sensor signal obtained from the first external electronic device;
obtaining, when the user's movement is not recognized based on the first motion sensor signal, the user's workout data based on a second motion sensor signal obtained from a second external electronic device; and
displaying the workout data on at least one of a display included in the electronic device or a display included in the first external electronic device.

18. The method of claim 17, wherein the first external electronic device and the second external electronic device are configured to obtain the first motion sensor signal and the second motion sensor signal, respectively according to the user's movement at different positions among the user's body parts.

19. The method of claim 17, further comprising:
identifying, when the user's movement is not recognized based on the second motion sensor signal, that both the first external electronic device and the second external electronic device provide an ultra-wide band (UWB) ranging; and
when the first external electronic device and the second external electronic device provide a UWB ranging function, controlling the first external electronic device and the second electronic device to perform, the UWB ranging between the first external electronic device and the second external electronic device to obtain distance information between the first external electronic device and the second external electronic device, and obtaining the user's workout data based on the distance information between the first external electronic device and the second external electronic device.

20. The method of claim 17, further comprising:
obtaining, when the user's movement is not recognized based on the second motion sensor signal, the user's workout data based on a barometric pressure sensor signal obtained through a barometric pressure sensor of the second external electronic device.

* * * * *